United States Patent
Singh et al.

(10) Patent No.: US 8,748,106 B2
(45) Date of Patent: Jun. 10, 2014

(54) METHODS OF IDENTIFYING A COMPOUND THAT INCREASES OR DECREASES THE INTERACTION OF HN-33 WITH SYNAPTOTAGMIN II

(75) Inventors: Bal Ram Singh, N. Dartmouth, MA (US); Yu Zhou, New Bedford, MA (US)

(73) Assignee: Bal Ram Singh, North Dartmouth, MA (US)

( * ) Notice: Subject to any disclaimer, the term of this patent is extended or adjusted under 35 U.S.C. 154(b) by 1101 days.

(21) Appl. No.: 11/911,889

(22) PCT Filed: Apr. 18, 2006

(86) PCT No.: PCT/US2006/014446
§ 371 (c)(1),
(2), (4) Date: May 20, 2008

(87) PCT Pub. No.: WO2006/113648
PCT Pub. Date: Oct. 26, 2006

(65) Prior Publication Data
US 2008/0226627 A1    Sep. 18, 2008

Related U.S. Application Data

(60) Provisional application No. 60/672,332, filed on Apr. 18, 2005.

(51) Int. Cl.
| | | |
|---|---|---|
| G01N 33/53 | (2006.01) | |
| G01N 33/567 | (2006.01) | |
| C07H 21/04 | (2006.01) | |
| C07H 19/00 | (2006.01) | |
| C07H 21/00 | (2006.01) | |
| C12N 15/00 | (2006.01) | |
| C12N 15/09 | (2006.01) | |
| C12N 15/10 | (2006.01) | |

(52) U.S. Cl.
USPC .......... 435/7.1; 435/455; 435/70.1; 435/6.16; 435/375; 435/6.13; 435/7.21

(58) Field of Classification Search
None
See application file for complete search history.

(56) References Cited

U.S. PATENT DOCUMENTS

| | | | |
|---|---|---|---|
| 6,994,859 B1 * | 2/2006 | Singh et al. | 424/247.1 |
| 2004/0191887 A1 * | 9/2004 | Chapman et al. | 435/252.3 |
| 2004/0219619 A1 | 11/2004 | Fernandez-Salas et al. | |
| 2005/0228169 A1 | 10/2005 | Yokota | |

FOREIGN PATENT DOCUMENTS

WO    WO 99/37326    7/1999

OTHER PUBLICATIONS

Burgess et al. J of Cell Bio. 1990, 111:2129-2138.*
Bowie et al. Science, 1990, 247:1306-1310.*
Pawson et al. 2003, Science 300:445-452.*
Chapman. Nat Rev Mol Cell Biol. Jul. 2002;3(7):498-508.*
Li et al. J. Nat. Toxins. 1998. 7: 215-226.*
Rummel et al. J. Biol. Chem. 2004, 279: 30865-30870.*
Zhou et al. FASEB J, May 14, 2004. vol. 18, No. 8, Suppl. S, pp. C69, Annual Meeting of the American Society for Biochemistry and Molecular Biology/8th Congress of the International Union for Biochemistry and Molecular Biology. Boston, MA, Jun. 12-14, 2004.*
International Search Report, PCT US06/14446, dated Sep. 5, 2008.
Sharma et al., "Enhancement of the Endopeptidase Activity of Purified Botulinum Neurotoxins A and E by an Isolated Component of the Native Neurotoxin Associated Proteins," Biochemistry 43:4791-4798 (2004).
Zhou et al., "Hemagglutinin-33 of type a botulinum neurotoxin complex binds with synaptotagmin II," FEBS Journal 272:2717-2726 (2005).
Written Opinion of the International Searching Authority for international patent application No. PCT/US06/14446, completed Aug. 12, 2008.
International Preliminary Report on Patentability for international patent application No. PCT/US06/14446, issued Mar. 10, 2009.

* cited by examiner

*Primary Examiner* — Chang-Yu Wang
(74) *Attorney, Agent, or Firm* — Sunstein Kann Murphy & Timbers LLP

(57) ABSTRACT

This application is based, inter alia, on the discovery of a binding interaction between the Hn-33 hemagglutinin polypeptide of the type A *Clostridium botulinum* neurotoxin complex and synaptosomal proteins, including synaptotagmin II (Syt II). Methods of screening for compounds that modulate, e.g., increase or decrease, this interaction are provided. Also provided are compositions and methods for targeting compounds to neuronal and cancer cells by coupling the compounds to Hn-33 or biologically active Hn-33 variants.

12 Claims, 8 Drawing Sheets

METHODS OF IDENTIFYING A COMPOUND THAT INCREASES OR DECREASES THE INTERACTION OF HN-33 WITH SYNAPTOTAGMIN II

CROSS-REFERENCE TO RELATED APPLICATION

This application is a national phase application filed under 35 U.S.C. 371 of International Application No. PCT/US2006/014446, filed Apr. 18, 2006, which claims the benefit of U.S. Ser. No. 60/672,332, filed on Apr. 18, 2005. The contents of this prior application is incorporated herein by reference in its entirety.

STATEMENT OF FEDERALLY SPONSORED RESEARCH

This invention was made with United States government support under grant number AI057159-01 awarded by the National Institutes of Health and grant number DAMD17-02-C-001 awarded by the Army Medical Research and Material Command. The United States government has certain rights in the invention.

FIELD OF THE INVENTION

The invention relates to a biologically active hemagglutinin protein from the *Clostridium botulinum* type A neurotoxin complex and interacting host proteins.

BACKGROUND

Botulinum neurotoxins (BoNTs) are extremely potent proteins with a mouse lethal dose of 0.3 ng/kg. Seven serotypes (A-G) of BoNTs are produced by different strains of *Clostridium botulinum*.

The mechanism by which BoNTs cause botulism has been well studied. After ingestion, the neurotoxin is translocated across the intestinal mucosa, gaining access to neuromuscular junctions. At affected junctions, the neurotoxin is internalized by neurons via endocytosis. Inside the cell, the protease activity of the toxin degrades specific vesicular and plasma membrane proteins, disrupting neurotransmitter release from the neuron. Thus, the patient experiences paralysis due to an inability to release neurotransmitters from the presynaptic surface.

SUMMARY

This application is based, inter alia, on the discovery of a binding interaction between a hemagglutinin polypeptide from the type A *Clostridium botulinum* neurotoxin complex, referred to herein as Hn-33, and synaptosomal proteins, including synaptotagmin II (Syt II). This application provides methods of screening for compounds that modulate, e.g., increase or decrease, this interaction. Also provided are compositions and methods for targeting compounds to neuronal cells by coupling the compounds to Hn-33.

The invention features methods of identifying compounds that modulate the interaction of Hn-33 with synaptosomal proteins. The methods include providing a first polypeptide that includes Hn-33 or a synaptosomal protein-binding variant thereof; providing a second polypeptide that includes a synaptosomal protein or an Hn-33-binding variant thereof; contacting the first and second polypeptides in the presence of a test compound; and determining an interaction (e.g., binding) between the first polypeptide and the second peptide. In some embodiments, a test compound that decreases an interaction between the first and second polypeptides is identified as a candidate inhibitor, and a test compound that increases an interaction between the first and second polypeptides is identified as a candidate potentiator. In some embodiments, the synaptosomal protein is a synaptotagmin, e.g., synaptotagmin II (Syt II).

The invention also features other methods of identifying compounds that modulate the interaction of Hn-33 with a synaptosomal protein. The methods include providing a cell that expresses, e.g., on the cell surface, a first polypeptide that includes a synaptosomal protein or an Hn-33-binding variant thereof; providing a second polypeptide that includes Hn-33 or a synaptosomal protein-binding variant thereof; contacting the cell with the second polypeptide in the presence of a compound; and determining an interaction of the second polypeptide with the cell (e.g., binding or internalization).

In some embodiments, a test compound that decreases an interaction between the second polypeptide and the cell is identified as a candidate inhibitor, and a test compound that increases an interaction between the first and second polypeptides is identified as a candidate potentiator. In some embodiments, the synaptosomal protein is a synaptotagmin, e.g., synaptotagmin II (Syt II). In some embodiments, the cell is a neuronal cell, e.g., a transformed neuronal cell such as a neuroblastoma cell (e.g., SH-SY5Y).

In another aspect, the invention features compositions that include Hn-33 or a variant thereof coupled to a non-botulinum neurotoxin compound or agent (e.g., any polypeptide, antibody, small molecule, enzyme, radioisotope, cytotoxic agent, contrast agent, or fluorophore other than a botulinum neurotoxin), such that the composition binds to a neuronal cell. In some embodiments, the composition binds to the synapse of a neuronal cell.

In another aspect, the invention features compositions that include Hn-33 coupled to a non-botulinum neurotoxin polypeptide (e.g., any antibody, antigen, or therapeutic protein other than a botulinum neurotoxin), such that the Hn-33 provides protease resistance to the polypeptide, e.g., by binding to the polypeptide.

In some embodiments, the invention features methods of targeting a compound to a neuronal cell in a subject. The methods include coupling a non-botulinum neurotoxin compound to Hn-33, thus providing a complex; and administering the complex to the subject. In certain embodiments, the invention features methods of administering a non-botulinum neurotoxin therapeutic protein to a subject. The methods include binding a non-botulinum neurotoxin protein, e.g., an antigen, a fusion protein or antibody (e.g., a human or humanized antibody), to Hn-33 or a biologically active variant thereof, thus providing a complex; and administering the complex to a subject, e.g., orally. In some embodiments, the invention features methods of immunizing a subject by administration (e.g., orally) of an antigen coupled to Hn-33 to a subject to elicit an immune response.

The invention also features methods of modulating Syt II function in a cell, e.g., in a subject, by contacting the cell with a sufficient amount of a polypeptide that includes Hn-33 or a biologically active variant thereof.

In another aspect, the invention features compounds that modulate, e.g., inhibit or strengthen, the interaction of Hn-33 with synaptosomal proteins, e.g., antibodies that bind to Hn-33 and/or Syt II. Also included are pharmaceutical and diagnostic formulations that include compositions described herein or candidate compounds identified by any of the methods described herein with a pharmaceutically acceptable excipient. These pharmaceutical formulations can either inhibit or strengthen the interaction of Hn-33 with a synaptosomal protein, e.g., Syt II.

The invention also features methods of treatment and diagnosis using the compositions described herein. In some aspects, the invention features methods of treating a subject afflicted with botulinum poisoning that include administering to the subject a composition that includes an inhibitor of an interaction (e.g., binding or internalization) between Hn-33 and synaptosomal proteins, e.g., Syt II. In some embodiments, the inhibitor of an interaction between Hn-33 and synaptosomal proteins is an antibody that binds to Hn-33, an antibody that binds to a synaptosomal protein (e.g., Syt II), an anti-idiotype antibody, a fragment or variant of Hn-33, or a fragment or variant of Syt II. In some aspects, the invention features methods of treating subjects with cancers, e.g., cancers that express synaptosomal proteins (e.g., leukemias such as mast cell leukemias and neuronal cancers such as neuroblastomas) that include administering to the subject a composition including Hn-33 or a fragment or variant thereof conjugated to a chemotherapeutic agent.

The invention also features methods of administering botulinum toxin to a subject, e.g., for therapeutic or cosmetic purposes, that include administering to the subject a purified composition that includes a purified Hn-33 polypeptide or a biologically active Hn-33 variant, e.g., before, after, or in conjunction with the administration of botulinum toxin. In some aspects, the invention features a composition, e.g., an injectable composition, that includes a botulinum toxin and a purified Hn-33 polypeptide or a biologically active variant thereof.

In some aspects, the invention features methods of administering botulinum toxin to a subject, e.g., for therapeutic or cosmetic purposes, that include administering to the subject a potentiator of an interaction between Hn-33 and a synaptosomal protein such as Syt II, e.g., before, after, or in conjunction with the administration of botulinum toxin. In some embodiments, the potentiator is a bispecific antibody that binds specifically to both Hn-33 and a synaptosomal protein such as Syt II. In some aspects, the invention features a composition, e.g., an injectable composition, that includes a botulinum toxin and a potentiator of an interaction between Hn-33 and synaptosomal proteins such as Hn-33.

In other aspects, the invention also features various uses of the compositions described herein in the manufacture of medicaments designed for various therapies. For example, the invention features uses of compositions described herein for the manufacture of a medicament for the treatment of cancer, for targeting non-botulinum neurotoxin compounds to neuronal cells in a subject, and uses of compositions including inhibitors of interactions between Hn-33 and synaptosomal proteins for the treatment of subjects afflicted with botulinum poisoning. In these uses, the synaptosomal protein can be synaptotagmin II, and the inhibitors can be selected from antibodies that bind to Hn-33, antibodies that bind to the synaptosomal protein, Hn-33 antibody anti-idiotype antibodies, biologically active Hn-33 variants, and biologically active synaptosomal protein variants.

A biologically active variant of a protein described herein is a polypeptide variant, e.g., a polypeptide having the amino acid sequence of a specific wild-type protein with one or more amino acid substitutions, deletions (e.g., a fragment), or insertions, or other modifications, that retains at least 50% of one or more biological activities of the wild-type protein. For example, a biologically active variant of Hn-33 is a polypeptide that has the amino acid sequence of Hn-33 (e.g., SEQ ID NO:1) with one or more amino acid substitutions, deletions, or insertions, and that retains at least 50% of the protease resistance, synaptosome protein (e.g., Syt II) binding, or internalization activity of wild-type Hn-33. A biologically active variant of Syt II is a polypeptide that has the amino acid sequence of SytII (e.g., SEQ ID NO:2) with one or more amino acid substitutions, deletions, or insertions, and that retains at least 50% of the Hn-33 binding activity of wild-type Syt II.

The term "cytotoxic agent" as used herein refers to a substance that inhibits or prevents the function of cells and/or causes destruction of cells. The term is intended to include radioactive isotopes (e.g., $^{131}$I, $^{125}$I, $^{90}$Y, and $^{186}$Re), chemotherapeutic agents, and toxins such as enzymatically active toxins of bacterial, fungal, plant or animal origin, or variants or fragments thereof.

The term "botulinum neurotoxin" as used herein refers to a neurotoxic protein complex produced by a *Clostridium botulinum* bacterium. A "non-botulinum neurotoxin compound" is any compound that is not a botulinum neurotoxin, and is not found naturally in a botulinum neurotoxin complex.

An "antigen" refers to a molecule containing one or more epitopes (either linear, conformational or both) that elicit an immunological response. The term is used interchangeably with the term "immunogen." Normally, a B-cell epitope will include at least about 5 amino acids, but can be as small as 3-4 amino acids. A T-cell epitope, such as a CTL epitope, will include at least about 7-9 amino acids, and a helper T-cell epitope has at least about 12-20 amino acids. The term "antigen" denotes both subunit antigens, i.e., antigens that are separate and discrete from a whole organism with which the antigen is associated in nature, as well as killed, attenuated, or inactivated bacteria, viruses, fungi, parasites, or other microbes. Antibodies such as anti-idiotype antibodies, or fragments thereof, and synthetic peptide mimotopes, which can mimic an antigen or antigenic determinant, are also captured under the definition of antigen as used herein A polypeptide or nucleic acid molecule "fragment" is a polypeptide or nucleic acid molecule that has the same consecutive sequence (e.g., amino acid or nucleic acid sequence) as a portion of a wild-type protein or nucleic acid molecule.

Unless otherwise defined, all technical and scientific terms used herein have the same meaning as commonly understood by one of ordinary skill in the art to which this invention belongs. Although suitable methods and materials for the practice or testing of the present invention are described below, other methods and materials similar or equivalent to those described herein, which are well known in the art, can also be used. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
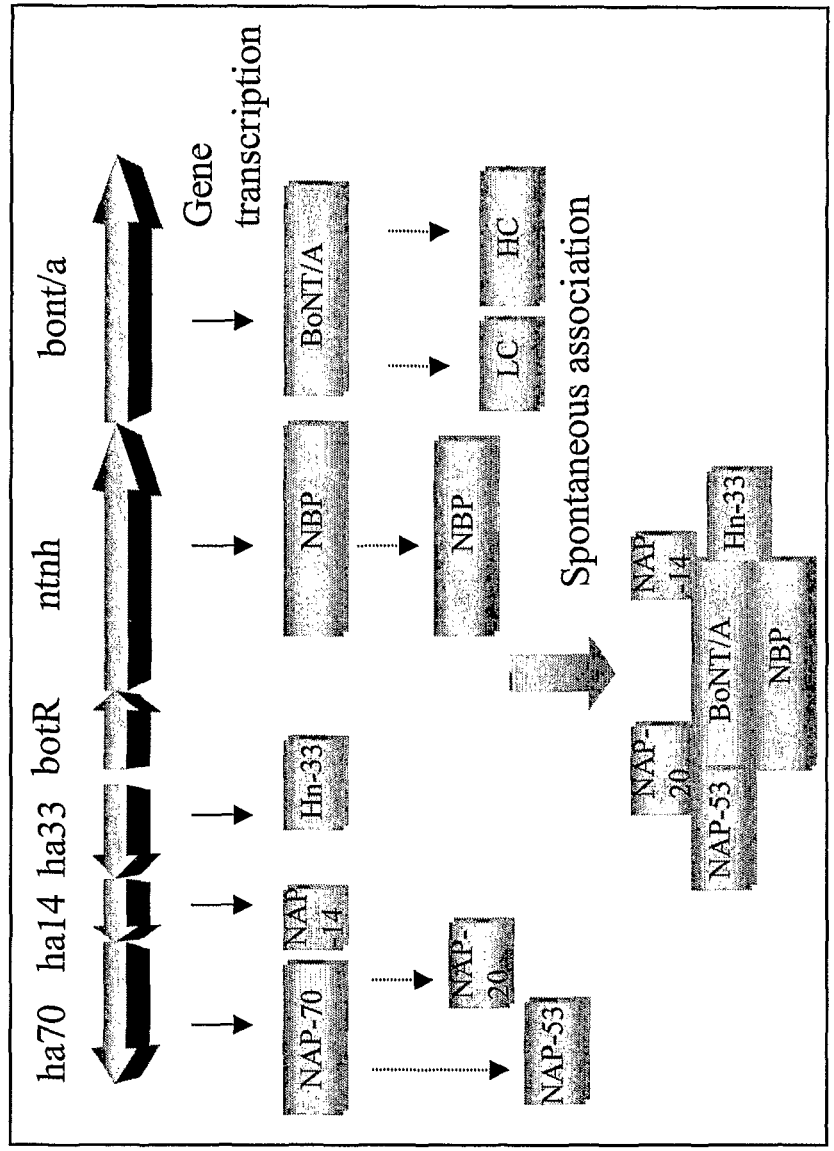
FIG. 1 is a depiction of the genetic organization of BoNT/A complex genes and their expressed proteins in forming the BoNT/A complex.

The present specification describes the discovery of an interaction between a hemagglutinin polypeptide from the type A *Clostridium botulinum* neurotoxin complex, referred to herein as Hn-33, and synaptosomal proteins, including synaptotagmin II (Syt II). Because Hn-33 interacts with synaptosomal proteins, Hn-33 can be used to target compounds, e.g., small molecules or proteins, to neuronal cells. Further, compounds that modulate the interaction between Hn-33 and Syt II can be useful therapeutically. For example, compounds that strengthen the interaction between Hn-33 and Syt II can be useful in potentiating the effects of botulinum neurotoxin (BoNT)-based therapies. Compounds that inhibit the interaction between Hn-33 and Syt II can be useful in treating the effects of botulism. Hn-33 can also provide protease resistance to associated proteins, e.g., in compositions.

Hn-33 Coupled to Compounds

In some embodiments, new compositions are made by coupling Hn-33 or a variant thereof to a compound, e.g., a polypeptide (e.g., an antigen), antibody or variant thereof, or a small molecule. These compositions can be used to target the compound to neuronal cells. These compositions can also be used such that the Hn-33 provides protease resistance to the coupled protein, such that the protein, e.g., a therapeutic protein, can be administered orally without being degraded by digestive enzymes.

Compounds can be coupled to Hn-33 either covalently or non-covalently. Methods of coupling compounds to proteins are well-known to skilled practitioners, and include the creation of fusion proteins, e.g., by providing a nucleic acid sequence that encodes a fusion protein that comprises Hn-33 and the desired polypeptide, and chemical conjugation, e.g., conjugation using maleimide, carbodiimide, N-hydroxysuccinimide, or glutaraldehyde. Compounds can be non-covalently coupled directly to Hn-33 by conjugation to a peptide that binds to Hn-33, e.g., an Hn-33 binding peptide of Syt II, BoNT/A, or BoNT/B, or indirectly by covalently coupling the Hn-33 to a moiety that facilitates a non-covalent interaction, e.g., biotin or streptavidin.

Compounds that can be targeted to neuronal cells using Hn-33 or biologically active variants thereof include neuroactive drugs, e.g. michellamine B, Q2-15, or N-Acetyl-CRA-TIKML-amide (Burnett et al., 2005, Bioorganic Med. Chem. 13:333-341; Schmidt and Stafford, 2000, FEBS Lett. 523: 423-426). By specifically targeting the compounds to neuronal cells, a smaller effective dose may be required to elicit the desired effect, which can decrease the side effects produced by administration of the compound.

Cytotoxic or chemotherapeutic agents can also be targeted (and/or internalized) to neuronal cells, e.g., cells of neuronal cancers such as neuroblastomas, by conjugation to Hn-33 or biologically active variants thereof. Many cytotoxic and chemotherapeutic agents act to inhibit cell division and these would be predicted to have little or no effect on non-dividing neuronal cells, while affecting dividing cancerous neuronal cells.

Chemotherapeutic drugs have different mechanisms by which they inhibit cancer. Chemotherapeutic drugs can damage the DNA template by alkylation, by cross-linking, or by double-strand cleavage of DNA. Other cancer drugs can block RNA synthesis by intercalation. Some agents are spindle poisons, such as vinca alkaloids, or anti-metabolites that inhibit enzyme activity, or hormonal and anti-hormonal agents. Chemotherapeutic drugs for targeting may be selected from various groups of agents, including but not limited to alkylating agents, antimetabolites, antitumor antibiotics, vinca alkaloids, epipodophyllotoxins, nitrosoureas, hormonal and antihormonal agents, and toxins.

Examples of chemotherapeutic agents include adriamycin, doxorubicin, epirubicin, 5-fluorouracil, cytosine arabinoside ("Ara-C"), cyclophosphamide, thiotepa, busulfan, cytoxin, taxoids, e.g., paclitaxel (TAXOL®, Bristol-Myers Squibb Oncology, Princeton, N.J.), and doxetaxel (TAXOTERE®, Rhone-Poulenc Rorer, Antony, France), toxotere, methotrexate, cisplatin, melphalan, vinblastine, bleomycin, etoposide, ifosfamide, mitomycin C, mitoxantrone, vincristine, vinorelbine, carboplatin, teniposide, daunomycin, caminomycin, aminopterin, dactinomycin, mitomycins, esperamicins (see U.S. Pat. No. 4,675,187), 5-FU, 6-thioguanine, 6-mercaptopurine, actinomycin D, VP-16, chlorambucil, melphalan, and other related nitrogen mustards. Also included in this definition are hormonal agents that act to regulate or inhibit hormone action on tumors such as tamoxifen and onapristone. Exemplary alkylating agents include cyclophosphamide, chlorambucil, busulfan, melphalan, thiotepa, ifosphamide, and nitrogen mustard. Exemplary antimetabolites include methotrexate, 5-Fluorouracil, cytosine arabinoside, 6-thioguanine, 6-mercaptopurin. Exemplary antitumor antibiotics include doxorubicin, daunorubicin, idorubicin, nimitoxantron, dactinomycin, bleomycin, mitomycin, and plicamycin. Exemplary vinca alkaloids and epipodophyllotoxins include vincristin, vinblastin, vindestin, etoposide, and teniposide. Exemplary nitrosoureas include carmustin, lomustin, semustin, and streptozocin. Exemplary hormonal and anti-hormonal agents include adrenocorticorticoids, estrogens, antiestrogens, progestins, aromatase inhibitors, androgens, and antiandrogens. Exemplary random synthetic agents include dacarbazin, hexamethylmelamine, hydroxyurea, mitotane, procarbazide, cisplastin, carboplatin.

Further, Hn-33 can be used to target various detectable agents to neuronal cells, e.g., for use in methods of diagnosis and imaging. Examples of detectable agents that can be coupled to Hn-33 or biologically active Hn-33 variants include various enzymes, prosthetic groups, fluorescent materials, contrast agents, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; examples of contrast agents include electron dense materials useful for electron microscopy, such as gold particles, or magnetically active materials useful for magnetic resonance imaging, such as supermagnetic iron particles; an example of a luminescent material includes luminol; examples of bioluminescent materials include luciferase, luciferin, and aequorin, and examples of suitable radioactive materials include $^{125}$I, $^{131}$I, $^{35}$S, and $^3$H. The coupled complexes can be used in standard diagnostic and imaging methods.

In addition, Hn-33 (and biologically active Hn-33 variants) naturally provides protease resistance to botulinum toxin proteins, e.g., BoNT/A. Hn 33 and biologically active Hn-33 variants can also be used to provide protease resistance to other bound polypeptides, e.g., therapeutic polypeptides, to be administered orally. Therapeutic proteins and peptides, e.g., hormones (e.g., insulin, human growth hormone), antibodies (e.g., etanercept, (EMBREL®, Immunex, Thousand Oaks, Calif.), infliximab (REMICADE®, Centocor, Malvern, Pa.), and adalimumab (HUMIRA®, Abbott Laboratories, Abbott Park, Ill.)), cytokines (e.g., IL-1, IL-2, IL-12, etc., (Xing and Wang, 2000, Current Pharmaceutical Design, 6:599-611)), and enzymes (e.g., Serrazyme; (BioMAX of Ohio, Le Mesa, Calif.)), are typically administered parenterally to avoid degradation in the digestive tract. These and other therapeutically useful proteins can be protected from degradation in the digestive tract by coupling the protein, e.g., covalently or non-covalently, to Hn-33 or a biologically active Hn-33 variant.

Screening Assays

In other embodiments, the invention provides methods (also referred to herein as "screening assays") for identifying modulators, i.e., candidate compounds or agents identified from one or more test compounds (e.g., proteins, peptides, peptidomimetics, peptoids, small inorganic molecules, small non-nucleic acid organic molecules, nucleic acids (e.g., antisense nucleic acids, siRNA, oligonucleotides, or synthetic oligonucleotides), or other drugs), that modulate the interaction between Hn-33 and synaptosomal proteins, e.g., Syt II. Test compounds thus identified are candidate compounds that can be used to modulate, e.g., increase or decrease, the binding of Hn-33 to Syt II, e.g., in a therapeutic protocol.

In one embodiment, assays are provided for screening test compounds to identify those that can modulate the binding of Hn-33 or a variant thereof to synaptosomal proteins, e.g., Syt II or variants thereof. Typically, synaptosomal proteins, e.g., Syt II polypeptides, can include at least part of the extracellular portion of the protein. For example, the N-terminal extracellular portion of Syt II can include amino acids 1 to 60, or a biologically active portion thereof. Compounds that modulate interaction of Hn-33 with synaptosomal proteins, e.g., Syt II, can be tested for their ability to potentiate or inhibit the effects of botulinum neurotoxin. Compounds that inhibit the interaction of Hn-33 with synaptosomal proteins can be useful for treatment of botulism, whereas compounds that strengthen the interaction of Hn-33 with synaptosomal proteins can be useful for therapeutic and cosmetic uses of botulism neurotoxins (e.g., onabotulinumtoxinA (BOTOX®, Allergan, Irvine, Calif.) and apobotulinumtoxinA (DYSPORT®, Ipsen, Paris, France).

The test compounds can be obtained using any approach in combinatorial library or other methods known in the art, including, but not limited to: biological libraries; peptoid libraries (libraries of molecules having the functionalities of peptides, but with a novel, non-peptide backbone, which are resistant to enzymatic degradation, but which, nevertheless, remain bioactive; see, e.g., Zuckermann et al., 1994, J. Med. Chem., 37:2678-2685); spatially addressable parallel solid phase or solution phase libraries; synthetic library methods requiring deconvolution; the "one-bead one-compound" library method; and synthetic library methods using affinity chromatography selection. The biological library and peptoid library approaches are limited to peptide libraries, while the other four approaches described above are applicable to peptide, non-peptide oligomer, or small molecule libraries of compounds (Lam, 1997, Anticancer Drug Des., 12:145).

Examples of methods for the synthesis of molecular libraries can be found in the art, for example in: DeWitt et al. (1993, Proc. Natl. Acad. Sci. USA, 90:6909; Erb et al., 1994, Proc. Natl. Acad. Sci. USA, 91:11422; Zuckermann et al., 1994, J. Med. Chem., 37:2678; Cho et al., 1993, Science, 261:1303; Carrell et al., 1994, Angew. Chem. Int. Ed. Engl., 33:2059; Carell et al., 1994, Angew. Chem. Int. Ed. Engl., 33:2061; and in Gallop et al., 1994, J. Med. Chem., 37:1233).

Libraries of compounds may be presented in solution (e.g., Houghten, 1992, Biotechniques, 13:412-421), or on beads (Lam, 1991, Nature, 354:82-84), chips (Fodor, 1993, Nature, 364:555-556), bacteria (Ladner, U.S. Pat. No. 5,223,409), spores (Ladner, U.S. Pat. No. 5,223,409), plasmids (Cull et al., 1992, Proc. Natl. Acad. Sci. USA, 89:1865-1869), or on phage (Scott and Smith, 1990, Science, 249:386-390; Devlin, 1990, Science, 249:404-406; Cwirla et al., 1990, Proc. Natl. Acad. Sci. USA, 87:6378-6382; Felici, 1991, J. Mol. Biol., 222:301-310; and Ladner supra).

In some embodiments, the assay is a cell-based assay in which a cell that expresses a synaptosomal protein, e.g., Syt II, or a biologically active portion thereof is contacted with a test compound, and the ability of the test compound to modulate Hn-33 binding is determined. The cell, for example, can be of mammalian origin, e.g., murine, rat, or human origin.

The ability of the test compound to modulate Hn-33 binding to a synaptosomal protein, e.g., Syt II, can be evaluated, for example, by coupling polypeptides, e.g., Hn-33 or Syt II, with a radioisotope, fluorescent tag, or enzymatic label such that binding of Hn-33 to Syt II can be determined by detecting the labeled polypeptide in a complex. For example, the polypeptides can be labeled with $^{125}$I, $^{35}$S, $^{14}$C, or $^3$H, either directly or indirectly, and the radioisotope detected by direct counting of radioemission or by scintillation counting. Alternatively, the polypeptides can be labeled with a fluorescent tag, e.g., a fluorescent protein, e.g., GFP or RFP. In other embodiments, the polypeptides can be enzymatically labeled with, for example, horseradish peroxidase, alkaline phosphatase, or luciferase, and the enzymatic label detected by determination of conversion of an appropriate substrate to product.

The ability of Hn-33 to interact with synaptosomal proteins, e.g., Syt II, with or without the labeling of any of the interactants can be evaluated. For example, a microphysiometer can be used to detect the interaction of Hn-33 with Syt II without labeling either polypeptide (McConnell et al., 1992, Science 257:1906-1912). As used herein, a "microphysiometer" (e.g., CYTOSENSOR®) is an analytical instrument that measures the rate at which a cell acidifies its environment using a light-addressable potentiometric sensor (LAPS). Changes in this acidification rate can be used as an indicator of the interaction between Hn-33 and Syt II.

In still other embodiments, a cell-free assay is provided in which an Hn-33 or synaptosomal protein, e.g., Syt II, or biologically active portion of either or both, is contacted with a test compound and the ability of the test compound to modulate the interaction of the polypeptides is evaluated. In general, biologically active portions of the Hn-33 and Syt II polypeptides to be used in the new assays include variants that participate in the interactions, e.g., variants that include a portion of the extracellular domain of Syt II.

Soluble and/or membrane-bound forms of isolated proteins (e.g., Hn-33 or synaptosomal proteins, e.g., Syt II, or biologically active portions thereof) can be used in cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, TRITON® X-100, TRITON® X-114, THESIT®, Isotridecypoly(ethylene glycol ether)n, 3-[(3-cholamidopropyl)dimethylammonio]-1-propane sulfonate (CHAPS), 3-[(3-cholamidopropyl)dimethylammonio]-2-hydroxy-1-propane sulfonate (CHAPSO), or N-dodecyl-N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

The interaction between Hn-33 and synaptosomal proteins, e.g., Syt II, can also be detected, e.g., using fluorescence energy transfer (FET) (see, for example, Lakowicz et al., U.S. Pat. No. 5,631,169 and Stavrianopoulos et al., U.S. Pat. No. 4,868,103). A fluorophore label on the first 'donor' molecule is selected such that its emitted fluorescent energy will be absorbed by a fluorescent label on a second 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor.' Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In other embodiments, determining the ability of the Hn-33 protein to bind to synaptosomal proteins, e.g., Syt II, can be accomplished using real-time Biomolecular Interaction Analysis (BIA) (e.g., Sjolander et al., 1991, Anal. Chem., 63:2338-2345 and Szabo et al., 1995, Curr. Opin. Struct. Biol., 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

In other embodiments, the target gene product, e.g., Hn-33 or Syt II, is anchored onto a solid phase. The target gene product/test polypeptide complexes anchored on the solid phase can be detected at the end of the reaction. The target gene product can be anchored onto a solid surface, and the test polypeptide, which is not anchored, can be labeled, either directly or indirectly, with detectable labels discussed herein. See, for example, Examples 2-4.

It may be desirable to immobilize Hn-33 or a synaptosomal protein, e.g., Syt II, or an anti-Hn-33 or anti-Syt II antibody, to facilitate separation of complexed from uncomplexed forms of one or both of the proteins, as well as to accommodate automation of the assay. Binding of Hn-33 to Syt II, or interaction of Hn-33 with Syt II in the presence or absence of a candidate compound, can be accomplished in any vessel suitable for containing the reactants. Examples of such vessels include microtiter plates, test tubes, and micro-centrifuge tubes. In one embodiment, a fusion protein can be provided that adds a domain that allows one or both of the proteins to be bound to a matrix. For example, glutathione-S-transferase/Hn-33 fusion proteins or glutathione-S-transferase/Syt II fusion proteins can be adsorbed onto glutathione SEPHAROSE® beads (Sigma Chemical, St. Louis, Mo.) or glutathione derivatized microtiter plates, which are then combined with the test compound or the test compound and either the non-adsorbed Hn-33 or Syt II protein, and the mixture incubated under conditions conducive to complex formation (e.g., at physiological conditions for salt and pH). Following incubation, the beads or microtiter plate wells are washed to remove unbound components, the matrix immobilized in the case of beads, complex determined either directly or indirectly, for example, as described above. Alternatively, the complexes can be dissociated from the matrix, and the level of binding determined using standard techniques.

Other techniques for immobilizing either Hn-33 or synaptosomal proteins, e.g., Syt II, on matrices include using conjugation of biotin and streptavidin. Biotinylated Hn-33 or Syt II protein can be prepared from biotin-NHS(N-hydroxy-succinimide) using techniques known in the art (e.g., biotinylation kit, Pierce Chemicals, Rockford, Ill.), and immobilized in the wells of streptavidin-coated 96 well plates (Pierce Chemical).

To conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In some embodiments, this assay is performed utilizing antibodies that bind specifically to Hn-33 or synaptosomal protein, e.g., Syt II, polypeptides, but do not interfere with binding of Hn-33 to the synaptosomal protein, e.g., Syt II. Such antibodies can be derivatized to the wells of the plate, and unbound Hn-33 or Syt II protein trapped in the wells by antibody conjugation. Methods for detecting such complexes, in addition to those described above for the GST-immobilized complexes, include immunodetection of complexes using antibodies reactive with Hn-33 or Syt II, as well as enzyme-linked assays which rely on detecting an enzymatic activity associated with the Hn-33 or Syt II, or antibodies thereto.

Alternatively, cell-free assays can be conducted in a liquid phase. In such an assay, the reaction products are separated from unreacted components, by any of a number of standard techniques, including but not limited to: differential centrifugation (for example, Rivas et al., 1993, Trends Biochem. Sci., 18:284-287); chromatography (gel filtration chromatography, ion-exchange chromatography); electrophoresis (e.g., Ausubel et al., eds., 1999, *Current Protocols in Molecular Biology*, J. Wiley: New York.); and immunoprecipitation (for example, Ausubel et al., eds., 1999, *Current Protocols in Molecular Biology*, J. Wiley: New York). Such resins and chromatographic techniques are known to those skilled in the art (e.g., Heegaard, 1998, J. Mol. Recognit., 11:141-148 and Hage et al., 1997, J. Chromatogr. B. Biomed. Sci. Appl., 699:499-525). Further, fluorescence energy transfer may also be conveniently utilized, as described herein, to detect binding without further purification of the complex from solution.

In some embodiments, the assay includes contacting the Hn-33 or synaptosomal protein, e.g., Syt II, or biologically active portion thereof with the other of Hn-33 or synaptosomal protein, e.g., Syt II, or biologically active portion thereof to form an assay mixture, contacting the assay mixture with a test compound, and determining the ability of the test compound to modulate binding of Hn-33 to Syt II, wherein determining the ability of the test compound to modulate binding of Hn-33 to Syt II includes determining proportions of bound Hn-33 and Syt II.

An Hn-33 protein can, in vivo, interact with one or more cellular or extracellular macromolecules, such as proteins, e.g., Syt II or other synaptosomal proteins. For the purposes of this discussion, such cellular and extracellular macromolecules are referred to herein as "binding partners." Compounds that disrupt such interactions can be useful in regulating the activity Hn-33 and BoNT. Such compounds can include, but are not limited to, molecules such as antibodies, peptides, and small molecules as described herein. In general, target genes/products for use in this embodiment are Hn-33 and Syt II. In alternative embodiments, the invention provides methods for determining the ability of the test compound to modulate the binding of Hn-33 to Syt II.

To identify compounds that interfere with the interaction between the Hn-33 and synaptosomal proteins, e.g., Syt II, a reaction mixture containing Hn-33 and the binding partner (e.g., Syt II) is prepared, under conditions and for a time sufficient, to allow the two products to form a complex. To test an inhibitory agent, the reaction mixture is provided in the presence and absence of the test compound. The test compound can be initially included in the reaction mixture, or can be added at a time subsequent to the addition of the target gene and its binding partner. Control reaction mixtures are incubated without the test compound or with a placebo. The formation of complexes between the target gene product and the binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant, but not normal, target gene products.

These assays can be conducted in a heterogeneous or homogeneous format. Heterogeneous assays involve anchoring either the Hn-33 (or variant thereof) or the binding partner (e.g., Syt II or a variant thereof) onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the Hn-33 and the binding partner, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the Hn-33 (or variant thereof) or the interactive binding partner (e.g., Syt II or a variant thereof), is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

To conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not prelabeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex formation or that disrupt preformed complexes can be identified.

In some cases, a homogeneous assay can be used. For example, a preformed complex of Hn-33 (or variant thereof) and the interactive binding partner (e.g., Syt II) is prepared in that either the Hn-33 or the binding partner is labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

Hn-33 Polypeptides Assays may be performed using a full-length Hn-33 polypeptide or a variant thereof. Likewise, compositions of the present invention can be created using a full-length Hn-33 polypeptide or a variant thereof. An exemplary Hn-33 amino acid sequence is hereby provided:

(SEQ ID NO: 1)
MEHYSVIQNSLNDKIVTISCKADTNLFFYQVAGNVSLFQQTRNYLER

WRLIYDSNKAAYKIKSMDIHNTNLVLTWNAPTHNISTQQDSNADNQY

WLLLKDIGNNSFIIASYKNPNLVLYADTVARNLKLSTLNNSNYIKFI

IEDYIISDLNNFTCKISPILDLNKVVQQVDVTNLNVNLYTWDYGRNQ

KWTIRYNEEKAAYQFFNTILSNGVLTWIFSNGNTVRVSSSNDQNNDA

QYWLINPVSDTDETYTITNLRDTTKALDLYGGQTANGTAIQVFNYHG

DDNQKWNIRNP

The sequences from about residue 164 to about residue 291 or about residue 174 to about residue 290, include two ricin-type beta-trefoil carbohydrate-binding domains. These domains are predicted to be important for binding to glycosylated portions of membrane proteins, e.g., synaptotagmins. Syt II, for example, contains a predicted N-glycosylation site. Exemplary biologically active variants, e.g., fragments, of Hn-33 (e.g., that bind to synaptosomal proteins) are fewer or greater than 60, 80, 100, 120, 140, 160, 180, 200, 220, 240, 260, or 280 amino acid residues in length and can include at least a portion of a ricin-type beta-trefoil carbohydrate-binding domain.

The gene that encodes Hn-33, ha33, is part of a cluster of neurotoxin-associated genes from *C. botulinum* (FIG. 1). Production and isolation of biologically active Hn-33 are described in U.S. application Ser. No. 09/546,727, the entire contents of which are hereby incorporated by reference.

Synaptosomal Proteins

As shown in Examples 1-5, Hn-33 binds to synaptosomal proteins including Syt II. As used herein, "synaptosomal proteins" are those proteins associated with isolated synaptosomes. Exemplary synaptosomal proteins include synaptotagmins (e.g., synaptotagmins 1-13), synaptosomal associated proteins (SNAPs), and SNAP receptors (SNAREs).

Synaptotagmins constitute a family of membrane-trafficking proteins that are characterized by an N-terminal transmembrane region, a variable linker, and two C-terminal $Ca^{2+}$-binding $C_2$-domains. An exemplary synaptotagmin II (Syt II) amino acid sequence is hereby provided:

(SEQ ID NO: 2)
MRNIFKRNQEPIVAPATTTATMPIGPVDNSTESGGAGESQEDMFAKL

KEKLFNEINKIPLPPWALIAIAVVAGLLLLTCCFCICKKCCCKKKKN

KKEKGKGMKNAMNNKDMKGGQDDDDAETGLTEGEGEGEEEKEPENLG

KLQFSLDYDFQANQLTVGVLQAAELPALDMGGTSDPYVKVFLLPDKK

KKYETKVHRKTLNPAFNETFTFKVPYQELGGKTLVMAIYDFDRFSKH

DIIGEVKVPMNTVDLGQPIEEWRDLQGGEKEEPEKLGDICTSLRYVP

TAGKLTVCILEAKNLKKMDVGGLSDPYGKIHLMQNGKRLKKKKTTVK

KKTLNPYFNESFSFEIPFEQIQKVQVVVTVLDYDKLGKNEAIGKIFV

GSNATGTELRHWSDMLANPRRPIAQWHSLKPEEEVDALLGKNK

The sequences from about residue 143 to about residue 261 and from about residue 271 to about residue 406, include two $C_2$ domains, also known as protein kinase C conserved region 2, subgroup 1 domains. The asparagine residue at position 29 is predicted to be glycosylated. Exemplary biologically active variants, e.g., fragments, of Syt II (e.g., that bind to Hn-33) are fewer or greater than 6, 8, 10, 12, 15, 20, 25, 30, 35, 45, 50, 55, or 60 amino acid residues in length.

Polypeptide Variants

Variants of Hn-33 and synaptosomal proteins differ from the naturally occurring, wild-type proteins in amino acid sequence or in ways that do not involve sequence, or both. Non-sequence modifications include in vivo or in vitro chemical derivatization of the protein. Non-sequence modifications also include changes in acetylation, methylation, phosphorylation, carboxylation, and/or glycosylation.

A biologically active variant of a polypeptide described herein retains at least 50%, e.g., 60%, 70%, 80%, 90%, or 95% of one or more biological activities of the wild-type polypeptide.

Typical variants include proteins, e.g., Hn-33 or biologically active fragments thereof, whose sequences differ from the wild-type sequence (e.g., SEQ ID NO:1) by one or more conservative amino acid substitutions or by one or more non-conservative amino acid substitutions, deletions, or insertions which do not abolish biological activity. In certain embodiments, the sequence can differ from wild-type sequence by 1 or fewer than 2, 3, 5, 10, 12, 15, but not more than 20 to 30 amino acid residues. In other embodiments, the variant is a portion or fragment of the polypeptide fewer or greater than 6, 8, 10, 12, 15, 20, 25, 30, 35, 45, 50, 55, 60, 80, 100, 120, 140, 160, 180, 200, 220, 240, 260, or 280 amino acid residues in length. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other conservative substitutions can be taken from the table below.

TABLE 1

CONSERVATIVE AMINO ACID REPLACEMENTS

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |

TABLE 1-continued

CONSERVATIVE AMINO ACID REPLACEMENTS

| For Amino Acid | Code | Replace with any of |
|---|---|---|
| Tyrosine | Y | D-Tyr, Phe, D-Phe, L-Dopa, His, D-His |
| Valine | V | D-Val, Leu, D-Leu, Ile, D-Ile, Met, D-Met |

Other variants are those with modifications that increase peptide stability; such analogs may contain, for example, one or more non-peptide bonds (which replace the peptide bonds) in the peptide sequence. Also included are: analogs that include residues other than naturally occurring L-amino acids, e.g., D-amino acids or non-naturally occurring or synthetic amino acids, e.g., β or γ amino acids; and cyclic analogs.

Amino acid sequence variants of a protein or nucleic acid that encodes a protein can be prepared by random mutagenesis of DNA that encodes a or a particular domain or region of a protein. Useful methods include PCR mutagenesis and saturation mutagenesis. A library of random amino acid sequence variants can also be generated by the synthesis of a set of degenerate oligonucleotide sequences.

The invention also provides for generation of mimetics, e.g., peptide or non-peptide agents based on Hn-33 or synaptosomal (e.g., Syt II) polypeptides. See, for example, "Peptide inhibitors of human papillomavirus protein binding to retinoblastoma gene protein" European patent applications EP-412,762A and EP-B31,080A.

Non-hydrolyzable peptide analogs of critical residues can be generated using benzodiazepine (e.g., see Freidinger et al. in *Peptides: Chemistry and Biology*, G. R. Marshall ed., ESCOM Publisher: Leiden, Netherlands, 1988), azepine (e.g., see Huffman et al. in *Peptides: Chemistry and Biology*, G. R. Marshall ed., ESCOM Publisher: Leiden, Netherlands, 1988), substituted gamma lactam rings (Garvey et al. in *Peptides: Chemistry and Biology*, G. R. Marshall ed., ESCOM Publisher: Leiden, Netherlands, 1988), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) *J Chem Soc Perkin Trans* 1:1231), and β-amino alcohols (Gordon et al. (1985) *Biochem Biophys Res Commun* 126:419; and Dann et al. (1986) *Biochem Biophys Res Commun* 134:71).

Fragments of Hn-33 or synaptosomal proteins can be produced in several ways, e.g., recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid which encodes the polypeptide. Expression of the mutagenized DNA produces polypeptide fragments. Digestion with "end-nibbling" endonucleases can thus generate DNA's which encode an array of fragments. DNA's which encode fragments of a protein can also be generated by random shearing, restriction digestion or a combination of the above-discussed methods.

Fragments can also be chemically synthesized using techniques known in the art such as conventional Merrifield solid phase f-Moc or t-Boc chemistry. For example, peptides of the present invention may be arbitrarily divided into fragments of desired length with no overlap of the fragments, or divided into overlapping fragments of a desired length.

Antibodies

The present invention also provides various antibodies, e.g., antibodies that inhibit the interaction between Hn-33 and synaptosomal proteins. The term "antibody" as used herein refers to an immunoglobulin molecule or immunologically active portion thereof, i.e., an antigen-binding portion. Examples of immunologically active portions of immunoglobulin molecules include F(ab) and $F(ab')_2$ fragments, which can be generated by treating the antibody with an enzyme such as pepsin.

Polypeptides described herein (or immunogenic fragments or analogs) can be used to raise antibodies. In general, the polypeptide can be coupled to a carrier protein such as KLH (as described in Ausubel et al., Current Protocols in Molecular Biology, John Wiley & Sons, New York, 1994), mixed with an adjuvant, and injected into a host mammal to produce polyclonal antibodies. These antibodies can be purified by antigen affinity chromatography. Polyclonal antibodies are heterogeneous populations of antibody molecules derived from the sera of the immunized animals.

In particular, various host animals can be immunized by injection with a biologically active Hn-33 protein. Host animals can include rabbits, mice, guinea pigs, and rats. Various adjuvants can be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum.*

The antibodies can be polyclonal, monoclonal, multispecific (e.g., bispecific), multifunctional (e.g., bifunctional), recombinant, e.g., chimeric or humanized, fully human, non-human, e.g., murine, or single chain antibodies. Methods of making such antibodies are known. In some cases, the antibodies have effector function and can fix complement. The antibodies can also be coupled to toxins, reporter groups, or imaging agents.

Chimeric, humanized, e.g., completely human, antibodies are desirable for applications that include repeated administration, e.g., therapeutic treatment (and some diagnostic applications) of a human subject. Therapeutic antibodies include etanercept (ENBREL®, Immunex, Thousand Oaks, Calif.), infliximab (REMICADE®, Centocor, Malvern, Pa.), and adalimumab (HUMIRA®, Abbott Laboratories, Abbott Park, Ill.). Methods of determining the activity elicited by a particular antibody can be determined using methods known in the art and methods described herein.

The antibody can be a single chain antibody. A single-chain antibody (scFV) may be engineered (for example, Colcher et al., 1999, Ann. N.Y. Acad. Sci., 880:263-280; and Reiter, 1996, Clin. Cancer Res., 2:245-252). The single chain antibody can be dimerized or multimerized to generate multivalent antibodies having specificities for different epitopes of the same target protein.

In some cases, the antibody has reduced or no ability to bind to an Fc receptor. For example, it is an isotype or subtype, fragment or other mutant, which does not support binding to an Fc receptor, e.g., it has a mutagenized or deleted Fc receptor binding region.

Monoclonal antibodies, which are homogeneous populations of antibodies to a particular antigen, can be prepared using the biologically active Hn-33 polypeptides described above and standard hybridoma technology (see, e.g., Kohler et al., Nature, 256:495, 1975; Kohler et al., Eur. J. Immunol., 6:511, 1976; Kohler et al., Eur. J. Immunol., 6:292, 1976;

Hammerling et al., In Monoclonal Antibodies and T Cell Hybridomas, Elsevier, N.Y., 1981; U.S. Pat. No. 4,376,110; Kosbor et al., Immunology Today, 4:72, 1983; Cole et al., Proc. Natl. Acad. Sci. USA, 80:2026, 1983; Cole et al., Monoclonal Antibodies and Cancer Therapy, Alan R. Liss, Inc., pp. 77-96, 1983; and Ausubel et al., *Current Protocols in Molecular Biology*, John Wiley & Sons, New York, 1994). Such antibodies can be of any immunoglobulin class including IgG, IgM, IgE, IgA, IgD and any subclass thereof. The hybridoma producing the Mab of this invention may be cultivated in vitro or in vivo.

In addition, techniques developed for the production of "chimeric antibodies" (Morrison et al., Proc. Natl. Acad. Sci. USA, 81:6851, 1984; Neuberger et al., Nature, 312:604, 1984; Takeda et al., Nature, 314:452, 1984) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine Mab and a human immunoglobulin constant region.

Alternatively, techniques described for the production of single chain antibodies (U.S. Pat. Nos. 4,946,778, 4,946,778, and 4,704,692) can be adapted to produce single chain antibodies against Hn-33 or other proteins. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments include, but are not limited to, F(ab')$_2$ fragments that can be produced by pepsin digestion of the antibody molecule, and Fab fragments that can be generated by reducing the disulfide bridges of F(ab')$_2$ fragments. Alternatively, Fab expression libraries can be constructed (Huse et al., Science, 246:1275, 1989) to allow rapid and easy identification of monoclonal Fab fragments with the desired specificity.

Antibodies to Hn-33 or other proteins can, in turn, be used to generate anti-idiotype antibodies that resemble a portion of the antigenic protein, using techniques well known to those skilled in the art (see, e.g., Greenspan et al., FASEB J., 7:437, 1993; Nissinoff, J. Immunol., 147:2429 1991). For example, antibodies that bind to biologically active Hn-33 and competitively inhibit the binding of a ligand of biologically active Hn-33 (e.g., O-nitropheny-β-D-galactoside or isopropyl-β-D-thiogalactoside) can be used to generate anti-idiotypes that resemble a ligand binding domain of biologically active Hn-33 and, therefore, bind and neutralize a ligand of biologically active Hn-33. Such neutralizing anti-idiotypic antibodies or Fab fragments of such anti-idiotypic antibodies can be used in therapeutic regimens.

A bispecific antibody is a molecule comprising two types of antibodies or antibody fragments having specificities for different antigens. The bispecific antibody is, not particularly limited, but can be a monoclonal antibody.

The bispecific antibodies described herein can be recombinant antibodies, generated using gene recombination techniques (see, e.g., Borrebaeck C A K and Larrick J W, Therapeutic Monoclonal Antibodies, Published in the United Kingdom by Macmillan Publishers Ltd, 1990). A recombinant antibody can be obtained by cloning an antibody-encoding DNA from antibody-producing cells, such as hybridomas or sensitized lymphocytes, incorporating the DNA into an appropriate vector, and introducing the vector into a host for antibody production.

Diabody refers to a bivalent antibody fragment constructed by gene fusion (Holliger P et al., Proc. Natl. Acad. Sci. USA 90: 6444-6448 (1993); EP 404,097; WO 93/11161; etc.). A diabody is a dimer comprising two peptide chains; in each polypeptide chain, an L chain variable region ($V_L$) is connected to an H chain variable region ($V_H$) on the same chain via a linker that is too short to allow paring between the two regions (for example, about 5 residues). $V_L$ and $V_H$ encoded on the same polypeptide chain form a dimer because they cannot form a single-stranded variable region fragment due to the short linker between them. Thus, a diabody ends up with two antigen binding sites.

An IgG type bispecific antibody can be secreted by a hybrid hybridoma (quadroma) formed by fusing two types of hybridomas that produce IgG antibodies (Milstein C et al., Nature 1983, 305: 537-540). It can also be secreted by introducing into cells genes of the L chains and H chains that constitute the two IgGs of interest (a total of four types of genes) for co-expression. However, theoretically, there are as many as ten combinations of H chains and L chains in the IgGs produced by these methods. It can be difficult to purify an IgG comprising the desired combination of H and L chains from ten different types of IgGs. Furthermore, in theory, the amount of the combination of interest is dramatically decreased, and thus large-scale cell culture is required, leading to a further increase in manufacturing cost.

By appropriately substituting amino acid(s) in the CH3 region of an H chain, it is possible to preferentially secrete IgGs that have a heterologous combination of H chains (Ridgway, J B et al. Protein Engineering 1996, 9: 617-621, Merchant, A M et al. Nature Biotechnology 1998, 16: 677-681).

As for L chains, an L chain variable region is less diverse compared to an H chain variable region; therefore, acquisition of a common L chain that provides binding activities with two H chains can be expected. Efficient expression of a bispecific IgG becomes possible by introducing genes of this common L chain and both of the H chains into a cell for IgG expression (Nature Biotechnology, 1998, 16, 677-681). In this respect, a method has been proposed for selection of a common L chain adapting arbitrary different H chains to show high binding ability (WO 2004/065611). An H chain having the above-described CH3 variant (Nature Biotechnology, 1998, 16, 677-681) is rarely secreted in the absence of the other H chain. By making use of this characteristic to first induce expression of the right-arm L chain and H chain and stop the expression, and then induce expression of the left-arm L chain and H chain, the proportion of IgGs expressed in the combination of interest may be increased (PCT/JP2004/008585).

A bispecific antibody can also be prepared by chemically cross-linking Fab's. A bispecific F(ab')$_2$ can be produced, for example, by maleimidating a Fab' prepared from one antibody with o-PDM (ortho-phenylenedi-maleimide) and reacting the product with a Fab' prepared from another antibody, so as to cross-link Fab's derived from different antibodies (Keler T et al. Cancer Research 1997, 57: 4008-4014). Further, a method for chemically connecting antibody fragments such as a Fab'-thionitrobenzoic acid (TNB) derivative and Fab'-thiol (SH) is also known (Brennan M et al., 1985. Science, 229: 81-83).

Instead of cross linkage, a leucine zipper derived from Fos and Jun or the like can be used. Although Fos and Jun also form a homodimer, their preferential heterodimer formation is utilized. A Fab' added with a Fos leucine zipper and a second Fab' added with a Jun leucine zipper are expressed for preparation. By mixing and reacting monomeric Fab'-Fos and Fab'-Jun, which have been reduced under mild conditions, a bispecific F(ab')$_2$ can be formed (Kostelny S A et al., 1992, J. Immunology, 148: 1547-53). This method is not limited to Fab' and can also be applied to scFv, Fv, etc.

A bispecific antibody can also be prepared in a form of diabody. A bispecific diabody is a heterodimer comprising two cross-over scFv fragments. That is, a bispecific diabody can be prepared by constructing a heterodimer using V$_H$(A)-V$_L$(B) and V$_H$(B)-V$_L$(A), which have been formed by connecting V$_H$ and V$_L$ derived from two types of antibodies: A and B, with a relatively short linker of about 5 amino acid residues (Holliger P et al. Proc. of the National Academy of Sciences of the USA 1993, 90: 6444-6448).

Construction of a bispecific diabody of interest can be promoted by performing appropriate amino acid substitutions (knobs-into-holes: Zhu Z et al. Protein Science. 1997, 6: 781-788) so as to link two types of scFv's with a flexible and relatively long linker of about 15 amino acid residues (a single-chain diabody: Kipriyanov S M et al. J. of Molecular Biology. 1999, 293: 41-56).

sc(Fv)$_2$ which can be prepared by linking two types of scFv's with a flexible and relatively long linker of about 15 amino acid residues can also become a bispecific antibody (Mallender W D et al. J. of Biological Chemistry, 1994, 269: 199-206).

Pharmaceutical Compositions

Once a candidate compound (or modulating agent) of interest has been identified, standard principles of medicinal chemistry can be used to produce derivatives of the compound. Derivatives can be screened for improved pharmacological properties, for example, efficacy, pharmaco-kinetics, stability, solubility, and clearance. The moieties responsible for a compound's activity in the assays described above can be delineated by examination of structure-activity relationships (SAR) as is commonly practiced in the art. A person of ordinary skill in pharmaceutical chemistry could modify moieties on a candidate compound or agent and measure the effects of the modification on the efficacy of the compound or agent to thereby produce derivatives with increased potency. For an example, see Nagarajan et al., *J. Antibiot.* 41:1430-8 (1988). Furthermore, if the biochemical target of the compound (or agent) is known or determined, the structure of the target and the compound can inform the design and optimization of derivatives. Molecular modeling software is commercially available (e.g., from Molecular Simulations, Inc.) for this purpose.

Compositions that include Hn-33 or variants thereof ("Hn-33 compositions") may be used for targeting compounds to neuronal cells or for preventing polypeptide degradation when combined with a pharmaceutically acceptable carrier. Such a composition may contain, in addition to the Hn-33 composition and carrier, various diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration.

In practicing the methods, a therapeutically effective amount of an Hn-33 composition can be administered to a subject, e.g., a mammal (e.g., a human). Hn-33 compositions may be administered alone or in combination with other therapies. When co-administered with one or more agents, the Hn-33 composition may be administered either simultaneously with the second agent, or sequentially. If administered sequentially, persons of skill in the art will be able to decide on the appropriate sequence of administering the Hn-33 composition in combination with other agents.

Administration of an Hn-33 composition to a subject can be carried out in a variety of conventional ways, such as oral ingestion, inhalation, or cutaneous, subcutaneous, or intravenous injection.

When an Hn-33 composition is administered orally, the composition can be in the form of a tablet, capsule, powder, solution or elixir. When administered in tablet form, the composition may additionally contain a solid carrier such as a gelatin or an adjuvant. A tablet, capsule, and powder may contain from about 5 to 95% carrier, and preferably from about 25 to 90% carrier. When administered in liquid form, a liquid carrier such as water, petroleum, oils of animal or plant origin such as peanut oil, mineral oil, soybean oil, or sesame oil, or synthetic oils may be added. The liquid form of the composition may further contain physiological saline solution (e.g., 0.9% sodium chloride), dextrose or other saccharide solution, or glycols such as ethylene glycol, propylene glycol or polyethylene glycol. When administered in liquid form, the pharmaceutical composition contains from about 0.5 to 90% by weight of carrier, and preferably from about 1 to 50% carrier.

When a therapeutically effective amount of an Hn-33 composition is administered by intravenous, cutaneous or subcutaneous injection, the carrier can be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to binding agent an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additive known to those of skill in the art.

The amount of an Hn-33 composition in the pharmaceutical compositions disclosed herein can be tailored by one skilled in the art. It is contemplated that the various pharmaceutical compositions of the present invention may about 0.01 µg to about 100 mg Hn-33 composition per kg body weight.

Applications

The new modulator compounds have a variety of uses. For example, potentiating agents can be used, e.g., to increase the potency and duration of effect of botulinum toxin, whether used therapeutically or for cosmetic purposes. Botulinum toxin (e.g., onabotulintoxinA (BOTOX®) or apobotulinumtoxinA (DYSPORT®)) can be used therapeutically, e.g., to treat cervical dystonia, blephorospasm and hemofacial spasm, other spasticity (e.g., due to stroke or cerebral palsy), spasmodic torticollis, strabismus, and primary axillary hyperhidrosis, and cosmetically, e.g., to reduce the appearance of wrinkles (e.g., glabellar lines). Typical dosages of botulinum toxin range from 0.1 to 1000 units per injection (e.g., 0.2, 0.5, 1, 2, 3, 4, 5, 10, 15, 20, 25, 50, 75, 100, 125, 150, 200, 250, or 500 units per injection), depending on the site, wherein one unit is the LD50 when injected intraperitoneally in mice.

Inhibiting compounds or agents as described herein can be used, e.g., to prevent or treat, e.g., ameliorate the symptoms of, potential or diagnosed botulism poisoning.

Compositions that include Hn-33 coupled to a detectable agent can be used in methods of imaging and diagnosis. The compositions are administered to a subject and the detectable agent is quantified, visualized, or detected by standard methods such as X-ray photography, magnetic resonance imaging, fluorescence imaging, or radiometry.

The compositions described herein that include a complex of an Hn-33 or biologically active Hn-33 variant coupled to a non-botulinum neurotoxin compound or agent, can be used for the manufacture of a medicament for the treatment of cancer, e.g., neuronal cancers, and for the manufacture of a medicament for targeting the non-botulinum neurotoxin compound to a neuronal cell in a subject.

EXAMPLES

The invention is further illustrated by the following examples. The examples are provided for illustrative purposes only. They are not to be construed as limiting the scope or content of the invention in any way.

Example 1

Isolation of Hn-33 Binding Protein from Synaptosomes

To identify and isolate Hn-33-interacting proteins from nerve cells, we prepared an affinity column of Hn-33, to which rat brain synaptosomal protein extract was applied. Hn-33, BoNT/A, and BoNT/A complex were purified from *Clostridium botulinum* type A (strain Hall) grown in N—Z amine medium (DasGupta and Sathyamoorthy, 1984, Toxicon. 22:415-24) using a series of chromatographic columns as described (Fu et al., 1998, J. Protein Chem. 7:53-60; Fu et al., 1998, Biochemistry 37:5267-5278). The purified Hn-33, BoNT/A and BoNT/A complex were precipitated with 0.39 g/ml ammonium sulfate and stored at 4° C. until use. The precipitate was centrifuged at 10,000×g for 10 minutes and dissolved in a desired buffer as needed for experiments.

Synaptosomes were prepared from frozen rat brains (RJO Biologicals Inc., Kansas City, Mo.) and solubilized with the addition of MEGA-9 (Nonanoyl-N-methylglucamide), which is non-ionic detergent, transparent in the UV region, and ideal for use as membrane protein solubilizers to the buffer, according to a previously published procedure (Li and Singh, 1998, J. Nat. Toxins 7:215-226).

The concentration of proteins used in the experiments was determined spectrophotometrically by measuring absorbance at 280 nm and 235 nm using the formula: concentration of protein mg/ml=(A235 nm−A280 nm)/2.51 (Whitaker and Granum, 1980, Anal. Biochem. 109:156-159).

Figure 2:
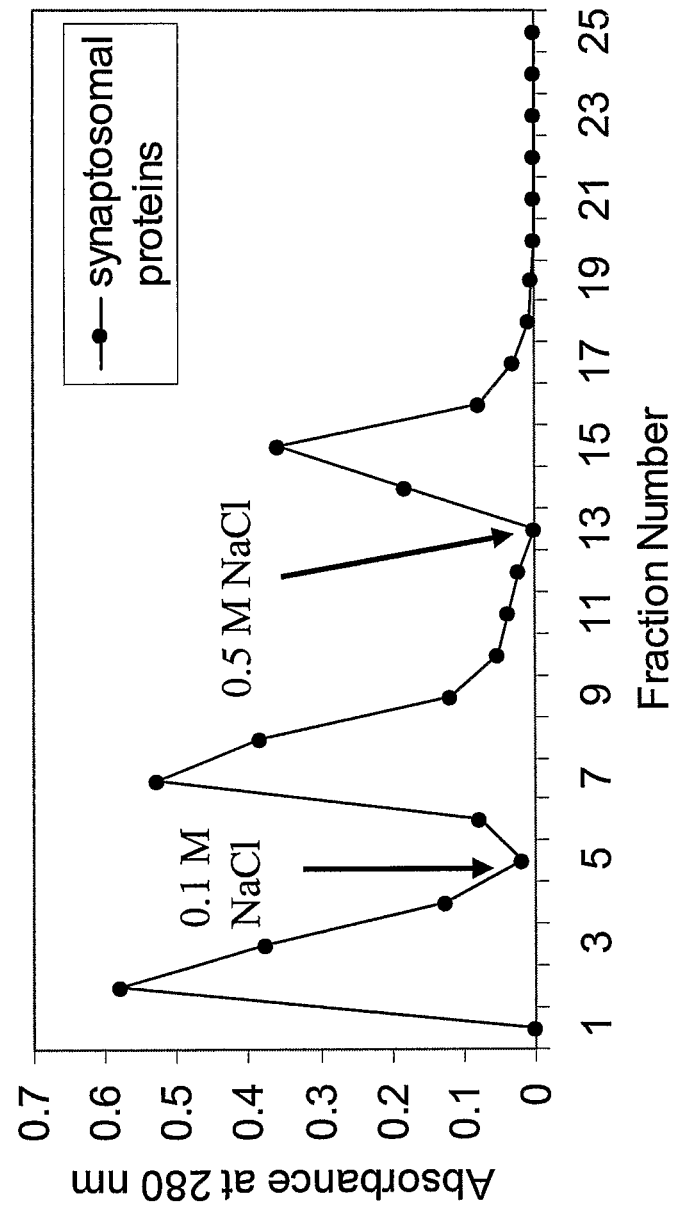
FIG. 2 is a line graph depicting the elution profile of solubilized synaptosomal proteins on Hn-33 affinity column. Protein content is indicated by absorbance at 280 nm. Arrows indicate application of the elution buffer. Each fraction collected was 1.5 ml.

FIG. 2 shows a representative elution profile of rat brain synaptosomal membrane proteins on an Hn-33 affinity column. Non-specifically adsorbed proteins and unbound rat brain synaptosomal membrane proteins were washed out with 10 mM Hepes buffer, pH 7.3 in fractions 3-5. Proteins bound to the Hn-33 affinity column were eluted with 10 mM Hepes buffer, pH 7.3, containing 0.1 M NaCl in fractions 7, 8, and 9; containing 0.5 M NaCl in fractions 14, 15, and 16. Analysis of 0.1 M NaCl eluate on reducing SDS-PAGE followed by Coomassie blue staining revealed five bands at about 180, 66, 50, 45, and 31 kDa. Analysis of the 0.5 M NaCl eluate on reducing SDS-PAGE revealed four protein bands with molecular masses of approximately 90, 55, 50 and 45 kDa. Western blot analysis using anti-synaptotagmin as primary antibody revealed that one band at 65 kDa of 0.1 M NaCl eluate is synaptotagmin, as indicated by comparison with a positive control of rat brain tissue extract and synaptosomal protein extract. Anti-synaptotagmin antibody did not react to any of the proteins eluted with 10 mM Hepes buffer, pH 7.3, containing 0.5 M NaCl.

Example 2

Synaptotagmin Binds to an Hn-33 Affinity Column

The binding nature of synaptotagmin to Hn-33 was further analyzed by preparing an affinity column of Hn-33, to which recombinant GST-Syt II was applied.

Recombinant glutathione S-transferase-fused full length of synaptotagmin II (GST-Syt II) was isolated as described (Zhou and Singh, 2004, Protein Expression and Purification 34:8-16).

Rabbit anti-Hn-33 antibody was obtained from BBTech (Dartmouth, Mass.), and sheep anti-rabbit IgG conjugated with FITC was purchased from Sigma (St. Louis, Mo.). Mouse anti-Syt antibody and goat anti-mouse IgG alkaline phosphatase conjugate were purchased from StressGen Biotechnologies (Victoria, BC, Canada) and Novagen (Madison, Wis.), respectively.

Hn-33 affinity column was prepared by coupling the purified Hn-33 to AFFI-GEL® 15 (Bio-Rad, Richmond, Calif.), an N-hydroxysuccinimide ester of cross-linked agarose. AFFI-GEL® 15 (1.5 ml) was washed 4 times each with 3 bed volumes of cold deionized water by centrifugation at 600 rpm for 30 sec at 4° C. The Hn-33 (1.5 mg) was dissolved in 1.5 ml coupling buffer (0.1 M bicarbonate buffer pH 8.3) and added to the washed Affi-Gel 15. After mixing them the mixture was incubated on a rotating platform at room temperature (25° C.) for 1 hour. One milliliter of 0.1 M ethanolamine, pH 8.0, was added into the mixture in order to block any remaining reactive groups, and the mixing continued for additional 1 hour under the same conditions. The Hn-33-conjugated gel was poured into a 1×10 cm glass column.

The following experiments were performed at 4° C. The Hn-33 affinity column was washed with 10 bed volumes of coupling buffer, and then 5 bed volumes of 10 mM Hepes buffer, pH 7.3, until absorbance at 280 nm was zero. The solubilized synaptosomal proteins (Li and Singh, 1998, J. Nat. Toxins 7:215-226) were applied to the column. Each sample was cycled through the affinity column five times to ensure maximum binding. The column was washed extensively with 10 mM Hepes buffer, pH 7.3 to remove non-specifically adsorbed proteins until absorbance at 280 nm was zero. Since the presence of detergent (MEGA-9) in washing buffer did not affect protein elution from the affinity column, the detergent was excluded from the washing buffer to avoid its interference in further assays of the eluted synaptotagmin. The column was eluted with 0.1 M NaCl in 10 mM Hepes buffer, pH 7.3, and then with 0.5 M NaCl in the same buffer, at flow rate of 1 ml/min and 1.5 ml fractions were collected. Absorbance at 280 nm was measured for each fraction; each fraction was mixed with reducing SDS-PAGE sample buffer (100 mM Tris-Cl, pH 6.8, 200 mM dithiothreitol, 4% SDS (electrophoresis grade), 0.2% bromophenol blue, 20% glycerol) and analyzed on a with 4-20% polyacrylamide gel. Fractions of 0.1 M NaCl eluate and 0.5 M NaCl eluate were analyzed by Western blot as described (Zhou and Singh, 2004, Protein Expression and Purification 34:8-16).

A similar experiment was carried out with full length of GST-Syt II and a control protein (GST, Sigma, St. Louis, Mo.) by applying them, separately, to the Hn-33-agarose affinity column. These experiments provided data to compare to the specific binding of Syt II to Hn-33. Fractions of 0.5 M NaCl eluate ere analyzed using Western blot as described (Zhou and Singh, 2004, Protein Expression and Purification 34:8-16).

For estimating protein bands of SDS-PAGE gels, the gels were scanned on a GEL LOGIC® 100 Imager system (Kodak, Rochester, N.Y.), plotted, and integrated for density using a KODAK 1D v.3.6.1 software (Kodak, Rochester, N.Y.).

Figure 3A:
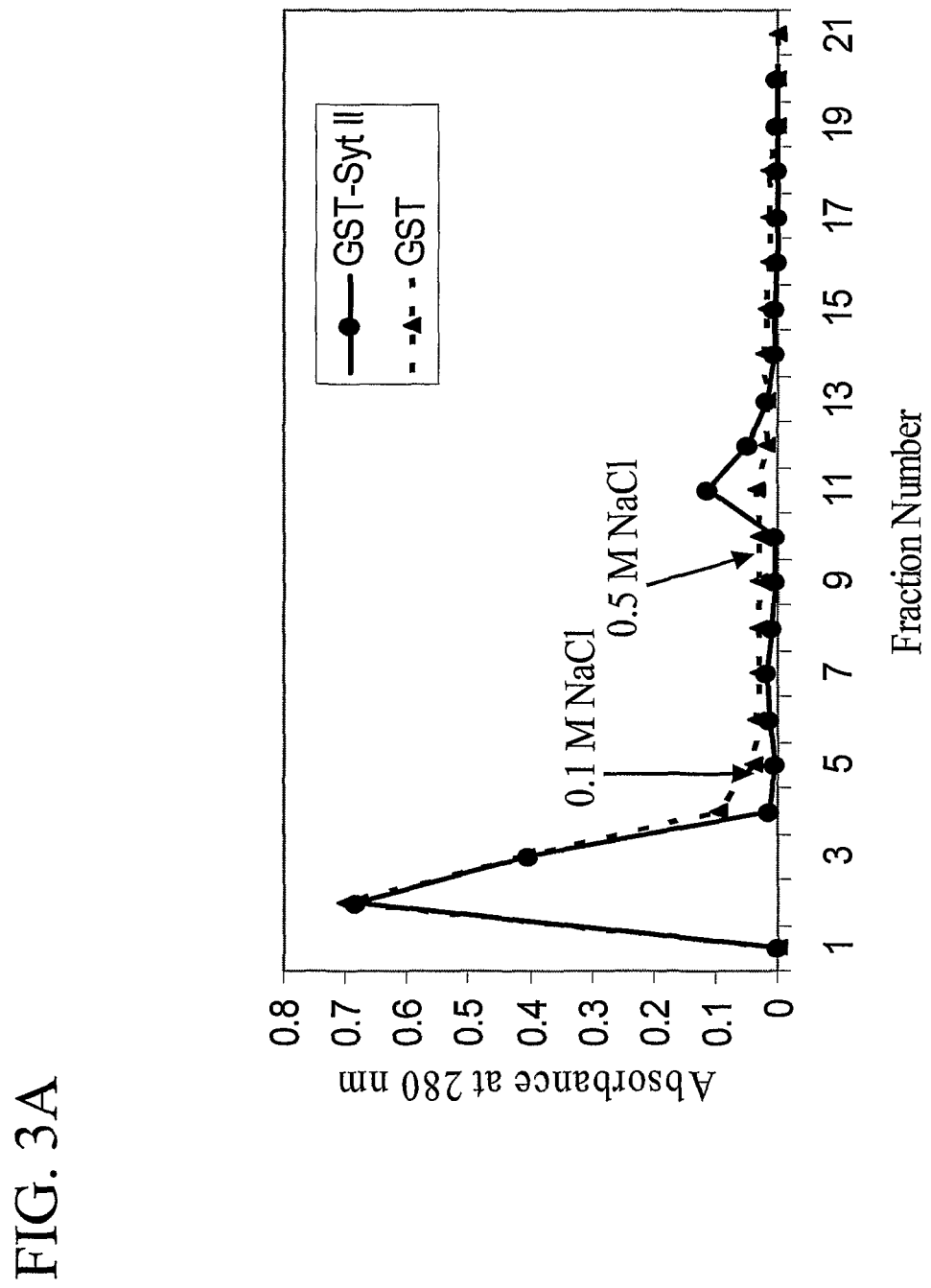
FIG. 3A is a line graph depicting the elution profiles of GST-Syt II and GST on Hn-33 affinity column. Protein content is indicated by absorbance at 280 nm. Arrows indicate application of the elution buffer. Each fraction collected was 1.5 ml.
Figures 3B, 3C:
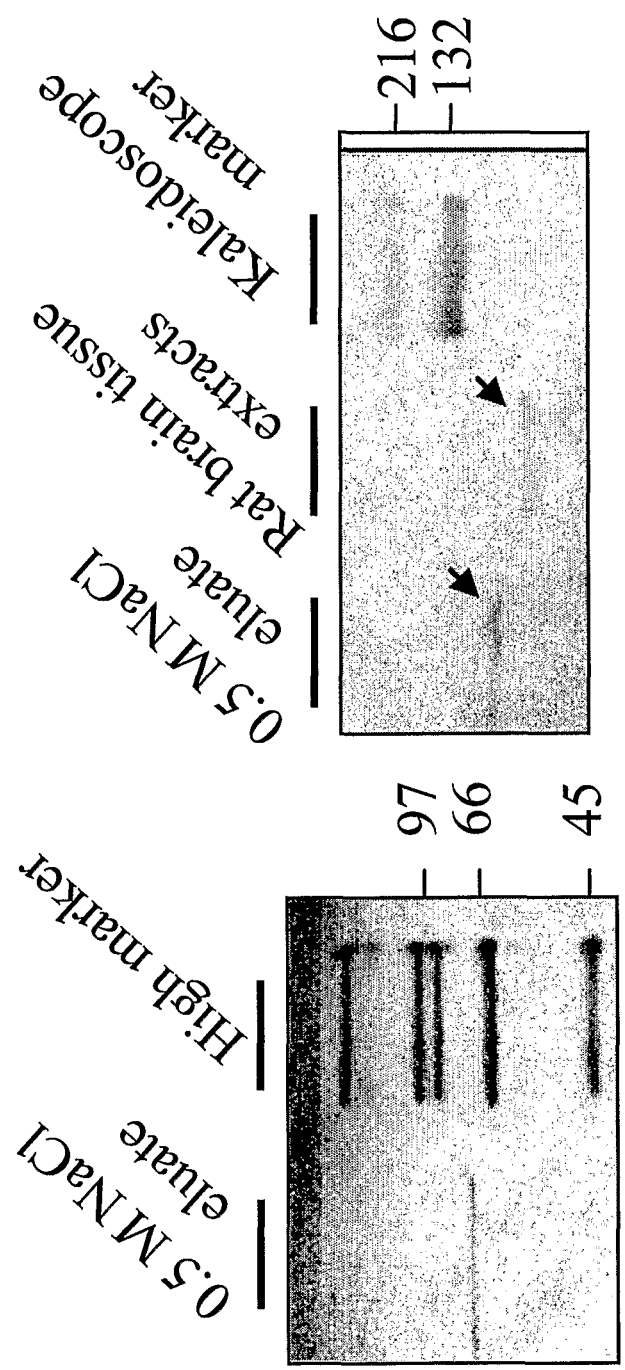
FIG. 3B is a reproduction of an SDS-PAGE gel of the 0.5 M NaCl eluate stained with Coomassie blue.
FIG. 3C is a reproduction of a Western blot analysis of elution peaks from the Hn-33 affinity column using rat anti-synaptotagmin antibody. Arrows indicate the positive bands, and the numbers indicate molecular mass of markers in kDa.
Figure 4A:
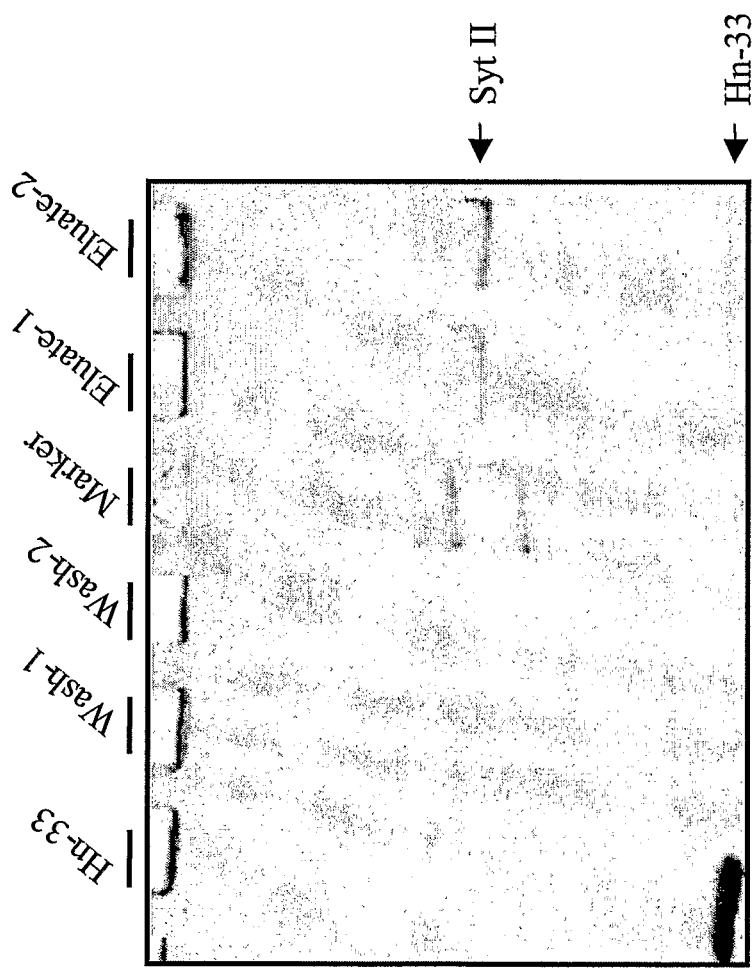
FIG. 4A is a reproduction of an SDS-PAGE gel of eluate from the GST-synaptotagmin II-SEPHAROSE® affinity column. The column was washed with PBS (Wash-1 and Wash-2) and eluted with 15 mM reduced glutathione in 50 mM Tris-HCl, pH 8.0, (Eluate-1, Eluate-2).
Figures 4B, 4C:
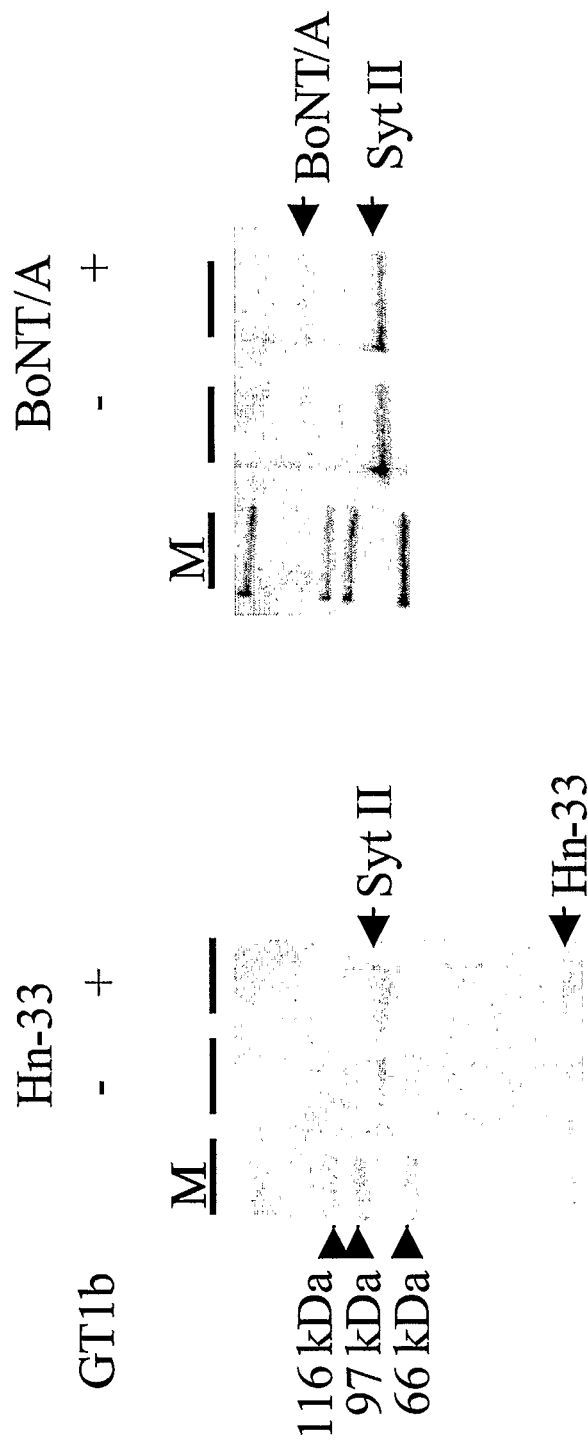
FIG. 4B is a reproduction of an SDS-PAGE gel of Hn-33 and Syt II-GST bound to glutathione-SEPHAROSE® beads.
FIG. 4C is a reproduction of an SDS-PAGE gel of BoNT/A and Syt II-GST bound to glutathione-SEPHAROSE® beads.
Figure 5A:
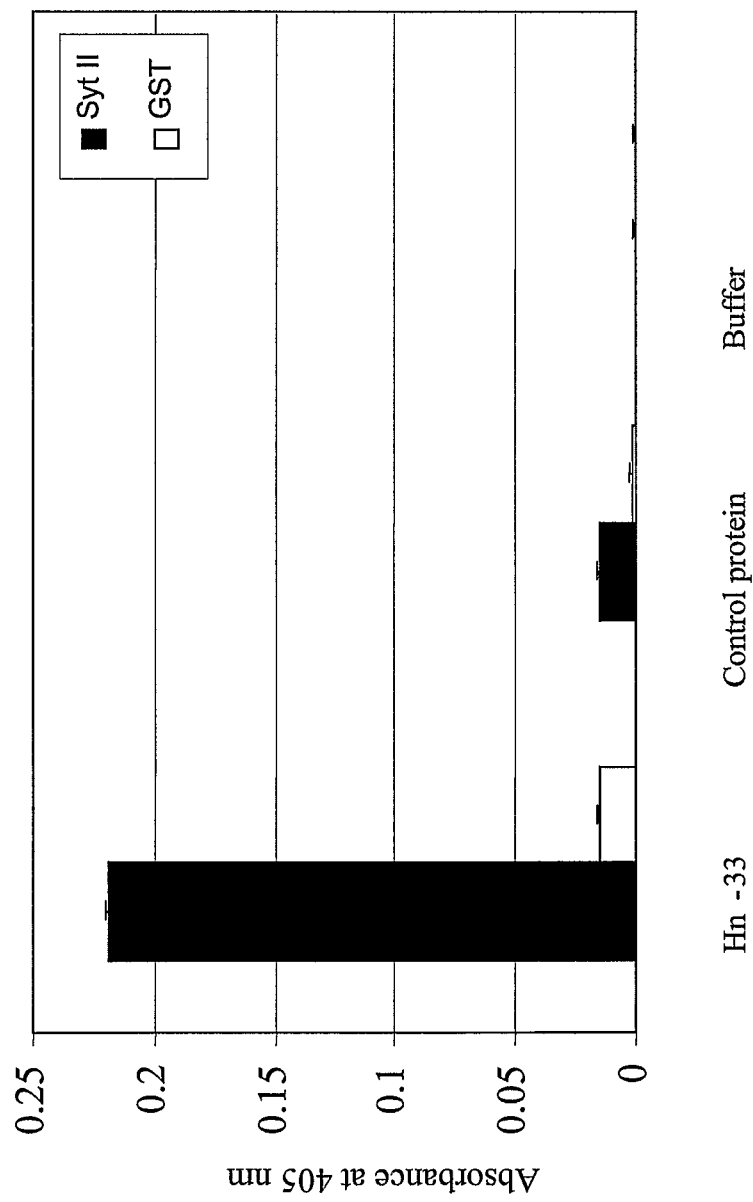
FIG. 5A is a bar graph that depicts the mean results of ELISA analysis of binding of Syt II to Hn-33. The results shown are mean of three separate experiments, each performed in triplicate; error bars represent the standard deviation.
Figure 5B:
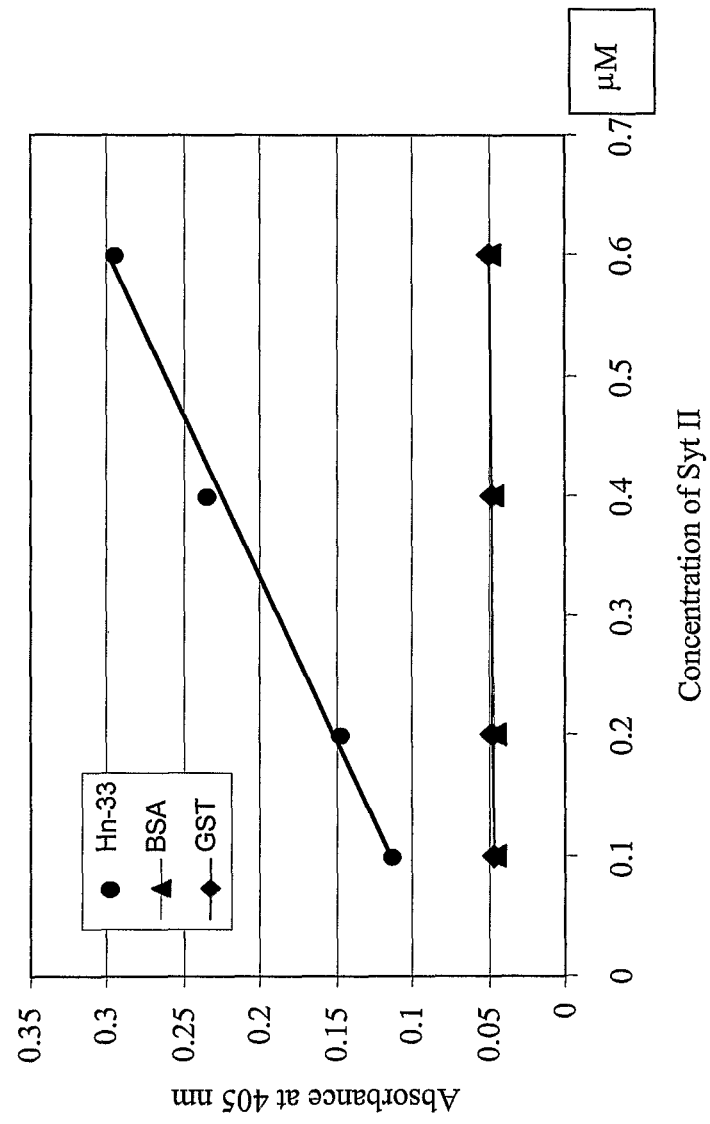
FIG. 5B is a graph depicting the concentration dependence of Hn-33 binding to Syt II.

A control experiment was carried out with GST alone applied to the Hn-33 affinity column. Affinity column chromatography was carried out in the same way as described for synaptosome extract. The elution profile obtained for GST-Syt II (FIG. 3A) shows only one elution peak that elutes with 0.5 M NaCl in 10 mM Hepes buffer, pH 7.3, whereas the control protein GST did not bind to the Hn-33 column (FIG. 3A). The Syt II binding to Hn-33 column was further confirmed by analyzing the eluate with a 4-20% SDS-PAGE (FIG. 3B) and Western blot (FIG. 3C). SDS-PAGE analysis showed a single protein band at about 90 kDa in the 0.5 M NaCl eluate, which corresponds to the molecular size of recombinant GST-synaptotagmin. Western blot analysis using anti-synaptotagmin as primary antibody revealed that the 0.5 M NaCl eluate of GST-Syt II is synaptotagmin II.

Example 3

Binding of Hn-33 to Synaptotagmin

Interaction of Hn-33 with synaptotagmin was further confirmed by immobilizing GST-synaptotagmin II on glutathione-SEPHAROSE® beads, and incubating the beads with Hn-33 in PBS buffer, pH 7.4. GST-synaptotagmin II immobilized on glutathione-SEPHAROSE® beads (1 ml, Amersham Pharmacia Biotech, Piscataway, N.J.) was incubated with 1 ml of Hn-33 (30.3 μM) in PBS buffer for 2 hours at 4° C. with gentle shaking. The mixture was then poured into a glass column (1.2 cm×8 cm). The column was washed with 10 bed volumes of PBS, and then eluted with 5 bed volumes of 50 mM Tris-HCl (pH 8.0), containing 15 mM reduced glutathione (Sigma). The eluates were analyzed using SDS-PAGE and were visualized by staining with Coomassie blue.

GST-synaptotagmin II immobilized on glutathione-SEPHAROSE® beads (1 ml, Amersham Pharmacia Biotech, Piscataway, N.J.) was incubated with 1 ml of Hn-33 (30.3 μM) in PBS buffer for 2 hours at 4° C. with gentle shaking. The mixture was then poured into a glass column (1.2 cm×8 cm). The column was washed with 10 bed volumes of PBS, and then eluted with 5 bed volumes of 50 mM Tris-HCl (pH 8.0), containing 15 mM reduced glutathione (Sigma). The eluates were analyzed using SDS-PAGE and were visualized by staining with Coomassie blue.

After washing, the bound materials were eluted with 15 mM reduced glutathione in 50 mM Tris-HCl (pH 8.0) and subjected to SDS-PAGE analysis. The GST-synaptotagmin II at 90 kDa and Hn-33 at 33 kDa were found in the eluate of bound material (FIG. 4A).

In a similar experiment, GST-synaptotagmin II immobilized to glutathione-SEPHAROSE® beads was used to precipitate Hn-33 (FIG. 4B) and BoNT/A (FIG. 4C). A pull-down assay was designed according to the procedure described previously (Sharma et al., 2003, Toxicon. 41:321-31; Dong et al., 2003, J. Cell Biol. 162:1293-1303) to confirm the binding of Hn-33 to synaptotagmin while using BoNT/A as a positive control. GST-synaptotagmin II was immobilized on glutathione-SEPHAROSE® beads (200 μl). The beads were then mixed with Hn-33 (18.0 μM) or BoNT/A (5.3 μM) in the absence (−) or presence (+; 12.5 μM) of ganglioside (GT1b) in 200 μA PBS (pH 7.4) for 1 hour at 4° C. Subsequently, beads were washed four times with PBS, until absorbance at 280 nm became zero. Bound proteins were solubilized by boiling in SDS sample buffer and analyzed by SDS-PAGE and Coomassie blue staining.

The results of the pull-down assay, as examined by the SDS-PAGE analysis, revealed that under identical conditions Hn-33 at concentration of 18.0 μM and BoNT/A at 5.3 μM bound substantially to Syt II, and these binding activities were independent of ganglioside (FIGS. 4B and 4C).

Example 4

ELISA Analysis of Syt II Binding to Hn-33

The binding of Syt II to Hn-33 was carried out in an ELISA format by coating Hn-33 in the wells, adding purified Syt II to each well, and then incubating the plate at RT (25° C.). ELISA was performed according to the procedure described previously (Zhou and Singh, 2004, Protein Expression and Purification 34:8-16). Briefly, 60 μl of 3.03 μM Hn-33 in coupling buffer (0.1 M bicarbonate, pH 8.3) and a control protein, GST (60 μl of 4.0 μM), were coated onto the wells of a polystyrene flat-bottomed 96-well microtiter plate (Corning Glass Works, Corning, N.Y.) and incubated at 4° C. overnight. After blocking the plate with 1% (w/v) bovine serum albumin (BSA, St. Louis, Mo.), 60 μl of the purified Syt II (1.1 μM) was added to the wells. Mouse anti-Syt antibody (StressGen Biotechnologies, Victoria, BC, Canada) and goat anti-mouse IgG alkaline phosphatase conjugate (Novagen, Madison, Wis.) were used as primary and secondary antibodies, respectively. The absorbance was measured using a microplate reader (GMI, Inc., Albertville, Minn.) and analyzed using Softmax software (Molecular Devices, Menlo Park, Calif.).

Similar experiments were carried out with GST alone, in place of GST-Syt II, to determine its nonspecific binding. Goat anti-GST antibody (Amersham Pharmacia Biotech, Piscataway, N.J.) and rabbit anti-goat IgG alkaline phosphatase conjugate (Sigma, St. Louis, Mo.) were used as primary and secondary antibodies, respectively.

The ELISA analysis with anti-Syt II antibody showed that Syt II binds to Hn-33 substantially (FIG. 5A). The Syt II did not bind to the control wells coated with GST (FIG. 5A). In a parallel study, it was shown that GST did not bind to Hn-33-coated plate (FIG. 5A).

Concentration-dependence of Syt II binding to Hn-33 is shown in FIG. 5B. Binding of different concentrations of Syt II was performed in the ELISA format described above. Syt II at different concentrations of 0.1, 0.2, 0.4, and 0.6 μM in PBS, pH 7.4 was added to the wells, which were coated with 3.03 μM Hn-33, or 1.5 μM BSA or 4.0 μM GST as control proteins.

The binding of Syt II to Hn-33 was linear within the concentration range of used (0.1-0.6 μM Hn-33). Linear regression of the binding curve yielded a slope of 0.27 $\mu M^{-1}$, suggesting a moderate binding of Syt II to Hn-33.

Example 5

Hn-33 Binds to Intact Synaptosomes

The binding of Hn-33 to synaptosomes was analyzed by immunofluorescence of bound Hn-33 using a rabbit anti-Hn-33 antibody and detecting the latter with FITC-labeled sheep anti-rabbit IgG.

Immunofluorescence staining was carried out on permeabilized synaptosomes using standard methods (Rothberg et al., 1992, Cell 68:673-82). This experiment was performed at room temperature (RT; about 25° C.), all the antibodies were diluted in PBS containing 3% BSA, and all washes were 5 times with PBST. The isolated synaptosomes were fixed on glass slides for 30 minutes with 4% paraformaldehyde (PFA) in PBS and permeabilized with 0.2% TRITON® X-100 for 15 minutes. The slides were washed and incubated with 3% BSA in PBS for 30 minutes, followed by incubation with 3.03 µM Hn-33 for 1 hour. After washing, the slides were incubated with rabbit anti-Hn-33 antibody serum (BBTech, Dartmouth, Mass.) for 30 minutes, washed, and then incubated with sheep anti-rabbit IgG conjugated with FITC (fluorescein-5-isothiocyanate). The slides were washed, and cover slips were mounted on them with a drop of FLUOROMOUNT-G® (Southern Biotechnology Associates, Inc., Birmingham, Ala.), according to the manufacturer's instructions. Fluorescence images were acquired with a Nikon Eclipse E600 MVI microscope equipped with a digital camera controlled by the software "SPOT" (Diagnostic Instruments. Inc., Sterling Heights, Mich.). One control experiment was carried out without incubating the synaptosomes with Hn-33, but incubating the synaptosomes directly with anti-rabbit IgG conjugated with FITC after blocking with 3% BSA.

Hn-33 was labeled with FITC using FLUOROTAG® FITC. Conjugation Kit from Sigma-Aldrich, and the inhibition of binding to synaptosomes of FITC-labeled Hn-33 by unlabeled Hn-33 was carried out similar to procedure described above. Briefly, after blocking the synaptosomes fixed on the glass slides with 3% BSA, followed by incubation with 18.0 µM Hn-33 for 30 minutes, the synaptosomes were then incubated with 18.0 µM, 9.0 µM, and 4.5 µM FITC-labeled Hn-33 for 1 hour. The slides were washed 5 times, cover slips were mounted, and then fluorescence images were observed under fluorescent microscope. The synaptosomes incubated with unlabeled Hn-33 and FITC-labeled Hn-33 separately were also carried out in parallel.

Only the synaptosomes incubated with Hn-33 showed a fluorescence signal. Negligible fluorescence signals appear in the synaptosomes without incubating with Hn-33, but incubating with only anti-rabbit IgG conjugated with FITC after blocking with 3% BSA.

Synaptosomes incubated with FITC-labeled Hn-33 showed strong signal even after 5 washes. However, preincubation of synaptosomes incubated with unlabeled Hn-33 even at 1:1 molar ratio blocked the binding of FITC-Hn-33, showing no fluorescence signal.

Example 6

Isolated, Biologically Active Hn-33 Binds to Type A Neurotoxin and Protects the Resulting Complex from Proteolytic Degradation Type A neurotoxin and Hn-33 were purified from *C. botulinum* type A as described (Fu et al., 1998, J. Protein Chem. 7:53-60; Fu et al., 1998, Biochemistry 37:5267-5278).

To determine direct binding between the neurotoxin and Hn-33, 5 mg of the neurotoxin was mixed with 1.7 mg Hn-33 in 3 ml 0.05 M sodium citrate, pH 5.5 (this corresponds to a 1:1.5 neurotoxin to Hn-33 molar ratio). The mixture was incubated for 30 minutes at room temperature before being applied to a SEPHADEX® G-200 column (1.5×100 cm) which was previously equilibrated with 0.05 M citrate buffer, pH 5.5. The protein was eluted with the same buffer at a flow rate of 12 ml/hour. The 1.7 ml fractions were collected, and the protein content was estimated by monitoring absorbance at 280 nm. Peak fractions were analyzed on 8-25% SDS-PAGE gels.

Two milligrams each of standard proteins (cytochrome C, 12.4 kDa; carbonic anhydrase, 29 kDa; BSA, 66 kDa; alcohol dehydrogenase, 150 kDa; and apoferritin, 443 kDa) were dissolved in 0.05 M sodium citrate, pH 5.5, and applied to SEPHADEX® G-200 column and eluted in the manner described immediately above. Blue dextran was run along with the standard proteins to estimate the void volume of the column. Molecular weights of the peaks corresponding to Hn-33 and its complex with neurotoxin were estimated using a plot of the log of standard MW vs. standard Rf value.

The Hn-33/neurotoxin mixture was eluted in two peaks. Peak fractions were subjected to SDS-PAGE, followed by Coomassie Blue staining, indicating that the first peak contained a 140 kDa and a 33 kDa protein and the second peak contained only the 33 kDa protein. Based on the 280 nm absorbance and the SDS-PAGE, it was estimated that about 94% of the Hn-33 bound to the neurotoxin.

Neurotoxin alone, neurotoxin complex, or equal amounts of neurotoxin and Hn-33 (which were mixed together and incubated for 30 minutes at room temperature), were dialyzed for 30 minutes in digestion buffer specific for each protease and then subjected to digestions. As expected, the neurotoxin complex remained at least 60% intact in digestions containing pepsin, trypsin, subtilisin, and α-chymotrypsin.

Pepsin began to digest the "naked" neurotoxin after 20 minutes and completely digested the neurotoxin after 60 minutes. When Hn-33 was included in the "naked" neurotoxin incubation, the neurotoxin remained at least 75% intact even after 90 minutes of digestion. Similar results were obtained when trypsin and chymotrypsin were used in separate experiments. These experiments indicate that Hn-33 can protect neurotoxins from proteolytic degradation under conditions which mimic the GI environment, including low pH and the presence epithelial cell surface carbohydrates. Thus, Hn-33 can protect associated proteins from proteolytic degradation.

Example 7

Screening for Modulators of Synaptosomal Protein-Hn-33 Interactions

Compounds that modulate the interaction of Hn-33 with synaptosomal proteins can be identified. Syt II is immobilized on a microtiter plate, and an excess of GFP-Hn-33 is added in the presence of a compound from a combinatorial library of small molecules. Following incubation and washing, the amount of fluorescence is measured, indicating the amount of bound GFP-Hn-33. Compounds that increase the interaction between Syt II and GFP-Hn-33 are identified as candidate potentiators and may be useful in BoNT therapeutics. Compounds that decrease the interaction between Syt II and GFP-Hn-33 are identified as candidate inhibitors and may be useful for treating botulism.

Example 8

Targeting Compounds to Neuronal Cells

Hn-33 can be used to target compounds to neuronal cells. A polypeptide is produced from a synthetic nucleic acid sequence that encodes the Hn-33 amino acid sequence with an amino-terminal extension that includes the amino acid sequence CRATKML (Schmidt et al., 1998, FEBS Lett. 435: 61-64) along with a linker containing one or more glycine resides. The peptide CRATKML has been shown to competitively inhibit the protease activity of BoNT. By targeting this peptide to neuronal cells, the peptide CRATKML should be more effective at inhibition of BoNT at lower administered concentrations.

Example 9

Binding and Internalization of Hemagglutinin-33 into a Human Neuroblastoma Cell Hn-33 was purified from *Clostridium botulinum* type A (strain Hall) grown in N—Z amine medium using a series of chromatographic columns as described by Fu et al., 1998, J. Protein Chem., 7:53-60. The purified Hn-33 was precipitated with 0.39 g/ml ammonium sulfate and stored at 4° C. until use. The precipitate was centrifuged at 10,000×g for 10 minutes and dissolved in a desired buffer as needed for experiments. The concentration of proteins was determined spectrophotometrically by measuring absorbance at 280 nm and 235 nm using the formula: concentration of protein (mg/ml)=$(A_{235}-A_{280})/2.51$ (Whitaker and Granum, 1980, Anal. Biochem., 109:156-159)

For preparation of FITC-labeled Hn-33, Hn-33 was labeled with FITC using FluoroTag™ FITC Conjugation Kit (Sigma-Aldrich), by the manufacturer's instructions.

Rabbit anti-Hn-33 antibody was obtained from BBTech (Dartmouth, Mass.), and sheep anti-rabbit IgG conjugated with FITC or TRITC was purchased from Sigma (St. Louis, Mo.). FITC-labeled goat anti-rabbit IgG and TRITC-labeled goat anti-rabbit IgG were purchased from Sigma (St. Louis, Mo.), respectively.

The human neuroblastoma cell line SH-SY5Y (Goodall et al., 1997, J. Neurochem., 68:1542-52; Purkiss et al., 2001, Neurotoxicology, 22:447-53) was purchased from the American Type Culture Collection (Manassas, Va.). The cells were grown in a 1:1 mixture of Eagle's Minimum Essential Medium with non-essential amino acids from ATCC (Manassas, Va.) and Ham's F12 medium from Sigma (St. Louis, Mo.) supplemented with 10% (v/v) fetal bovine serum (ATCC, Manassas, Va.) at 37° C., in a humidified incubator with 10% $CO_2$.

SH-SY5Y cells were grown in slide-culture flasks (Nunc A/S, Roskilde, Denmark) for two days and then were washed twice with fresh culture medium.

For binding assays, the cells were incubated with Hn-33 at concentrations of 30, 55, 110, and 220 nM in the culture medium, at 37° C. for 5 minutes.

For internalization assays, the cells were incubated with 30 n4 Hn-33 in the culture medium, at 37° C. for 5 minutes, and the medium containing Hn-33 was removed. The cells were then rinsed with fresh culture medium and incubated in fresh medium at 37° C. for 5, 10, or 15 minutes before analysis.

Immunofluorescence staining was carried out as above. Rabbit anti-Hn-33 antibody was used as primary antibody and Anti-rabbit IgG FITC-conjugate (green) and anti-rabbit IgG TRITC-conjugate (red) were used as secondary antibodies. After incubation of the cells in the conditions mentioned above, the cells were washed with PBS twice, fixed with 3.7% formaldehyde for 15 minutes, quenched with 50 mM $NH_4Cl$ for 10 minutes, and then blocked with 2% BSA for 60 minutes at room temperature. To observe the binding of Hn-33, the fixed cells were treated with rabbit anti-Hn-33 serum for 60 minutes, followed by TRITC-labeled goat anti-rabbit IgG for 30 minutes. To observe the internalization of Hn-33, the fixed cells were treated with rabbit anti-Hn-33 serum for 60 minutes, followed by FITC-labeled goat anti-rabbit IgG for 30 minutes.

Confocal microscopy (Zeiss 410 confocal laser scanning Leica TCS SP2 AOBS spectral confocal microscope, RENAISSANCE™ software from Microcosm, Columbia, Md.) was used to observe the fluorescence signals.

The binding capability of Hn-33 to SH-SY5Y cells was studied using concentrations of Hn-33 at 30, 55, 110, 220 nM. The binding of Hn-33 to the surface of the SH-SY5Y cells was observed under confocal microscope after incubation of 30 nM or more Hn-33 with SH-SY5Y cells. Binding of Hn-33 to the plasma membrane of SH-SY5Y cells was observed after a 5 minute incubation of Hn-33 with the cells.

To examine the internalization of Hn-33, SH-SY5Y cells were exposed to Hn-33 for 5 minutes, incubated without Hn-33 for 5, 10, or 15 minutes, and then observed using confocal laser scanning microscopy. Hn-33 was clearly observed inside the plasma membrane after a 15 minute incubation of Hn-33 with the cells.

This example demonstrates that neuroblastoma cells have receptor(s) for Hn-33 on the cell surface and a mechanism for the uptake of Hn-33.

Other Embodiments

A number of embodiments of the invention have been described. Nevertheless, it will be understood that various modifications may be made without departing from the spirit and scope of the invention. Accordingly, other embodiments are within the scope of the following claims.

---

What is claimed is:

1. A method of identifying a compound that increases the interaction of a hemagglutinin polypeptide from the type A *Clostridium botulinum* neurotoxin complex (Hn-33) with a synaptotagmin II polypeptide, wherein the Hn-33 polypeptide is capable of binding to the synaptotagmin II polypeptide, the method comprising:
   providing an Hn-33 polypeptide comprising amino acids 174 to 290 of SEQ ID NO: 1 and at least 95% identical to SEQ ID NO: 1;
   providing a synaptotagmin II polypeptide comprising the sequence of SEQ ID NO: 2;
   contacting the Hn-33 polypeptide and the synaptotagmin II polypeptide in the presence of a test compound; and
   determining a change in the binding between the Hn-33 polypeptide and the synaptotagmin II polypeptide in the presence of the test compound compared to the binding in the absence of the test compound, wherein an increase in the binding indicates that the compound increases the interaction of the Hn-33 polypeptide with the synaptotagmin II polypeptide.

2. The method of claim 1, wherein the synaptotagmin II polypeptide is expressed on the surface of a cell, contacting the Hn-33 polypeptide and the synaptotagmin II polypeptide in the presence of a test compound comprises contacting the cell with the Hn-33 polypeptide in the presence of a test compound, and wherein determining a change in the binding between the Hn-33 polypeptide and the synaptotagmin II polypeptide comprises determining a change in the binding between the Hn-33 polypeptide and the cell in the presence of the test compound.

3. The method of claim 1, wherein the Hn-33 polypeptide comprises the sequence of SEQ ID NO: 1.

4. The method of claim 1, wherein the Hn-33 polypeptide is a fusion protein.

5. The method of claim 2, wherein the Hn-33 polypeptide comprises the sequence of SEQ ID NO: 1.

6. The method of claim 2, wherein the Hn-33 polypeptide is a fusion protein.

7. A method of identifying a compound that decreases the interaction of a hemagglutinin polypeptide from the type A Clostridium botulinum neurotoxin complex (Hn-33) with a synaptotagmin II protein, wherein the Hn-33 polypeptide is capable of binding to the synaptotagmin II polypeptide, the method comprising:

provinding an Hn-33 polypeptide comprising amino acids 174 to 290 of SEQ ID NO: 1 and at least 95% identical to SEQ ID NO: 1;

providing a synaptotagmin II polypeptide comprising the sequence of SEQ ID NO: 2;

contacting the Hn-33 polypeptide and the synaptotagmin II polypeptide in the presence of a test compound; and determining a change in the binding between the Hn-33 polypeptide and the synaptotagmin II polypeptide in the presence of the test compound compared to the binding in the absence of the test compound, wherein a decrease in the binding indicates that the compound decreases the interaction of the Hn-33 polypeptide with the synaptotagmin II polypeptide.

8. The method of claim 7, wherein the Hn-33 polypeptide comprises the sequence of SEQ ID NO: 1.

9. The method of claim 7, wherein the Hn-33 polypeptide is a fusion protein.

10. The method of claim 7, wherein the synaptotagmin II polypeptide is expressed on the surface of a cell, contacting the Hn-33 polypeptide and the synaptotagmin II polypeptide in the presence of a test compound comprises contacting the cell with the Hn-33 polypeptide in the presence of a test compound, and wherein determining a change in the binding between the Hn-33 polypeptide and the synaptotagmin II polypeptide comprises determining a change in the binding between the Hn-33 polypeptide and the cell in the presence of the test compound.

11. The method of claim 10, wherein the Hn-33 polypeptide comprises the sequence of SEQ ID NO: 1.

12. The method of claim 10, wherein the Hn-33 polypeptide is a fusion protein.

\* \* \* \* \*

SEQUENCE LISTING

```
<160> NUMBER OF SEQ ID NOS: 2

<210> SEQ ID NO 1
<211> LENGTH: 293
<212> TYPE: PRT
<213> ORGANISM: Clostridium botulinum

<400> SEQUENCE: 1

Met Glu His Tyr Ser Val Ile Gln Asn Ser Leu Asn Asp Lys Ile Val
1               5                   10                  15

Thr Ile Ser Cys Lys Ala Asp Thr Asn Leu Phe Phe Tyr Gln Val Ala
            20                  25                  30

Gly Asn Val Ser Leu Phe Gln Gln Thr Arg Asn Tyr Leu Glu Arg Trp
        35                  40                  45

Arg Leu Ile Tyr Asp Ser Asn Lys Ala Ala Tyr Lys Ile Lys Ser Met
    50                  55                  60
```

```
Asp Ile His Asn Thr Asn Leu Val Leu Thr Trp Asn Ala Pro Thr His
 65                  70                  75                  80

Asn Ile Ser Thr Gln Gln Asp Ser Asn Ala Asp Asn Gln Tyr Trp Leu
             85                  90                  95

Leu Leu Lys Asp Ile Gly Asn Asn Ser Phe Ile Ile Ala Ser Tyr Lys
        100                 105                 110

Asn Pro Asn Leu Val Leu Tyr Ala Asp Thr Val Ala Arg Asn Leu Lys
        115                 120                 125

Leu Ser Thr Leu Asn Asn Ser Asn Tyr Ile Lys Phe Ile Ile Glu Asp
        130                 135                 140

Tyr Ile Ile Ser Asp Leu Asn Asn Phe Thr Cys Lys Ile Ser Pro Ile
145                 150                 155                 160

Leu Asp Leu Asn Lys Val Val Gln Gln Val Asp Val Thr Asn Leu Asn
                165                 170                 175

Val Asn Leu Tyr Thr Trp Asp Tyr Gly Arg Asn Gln Lys Trp Thr Ile
            180                 185                 190

Arg Tyr Asn Glu Glu Lys Ala Ala Tyr Gln Phe Phe Asn Thr Ile Leu
        195                 200                 205

Ser Asn Gly Val Leu Thr Trp Ile Phe Ser Asn Gly Asn Thr Val Arg
        210                 215                 220

Val Ser Ser Asn Asp Gln Asn Asn Asp Ala Gln Tyr Trp Leu Ile
225                 230                 235                 240

Asn Pro Val Ser Asp Thr Asp Glu Thr Tyr Thr Ile Thr Asn Leu Arg
                245                 250                 255

Asp Thr Thr Lys Ala Leu Asp Leu Tyr Gly Gly Gln Thr Ala Asn Gly
            260                 265                 270

Thr Ala Ile Gln Val Phe Asn Tyr His Gly Asp Asp Asn Gln Lys Trp
        275                 280                 285

Asn Ile Arg Asn Pro
        290

<210> SEQ ID NO 2
<211> LENGTH: 419
<212> TYPE: PRT
<213> ORGANISM: Homo sapiens

<400> SEQUENCE: 2

Met Arg Asn Ile Phe Lys Arg Asn Gln Glu Pro Ile Val Ala Pro Ala
  1               5                  10                  15

Thr Thr Thr Ala Thr Met Pro Ile Gly Pro Val Asp Asn Ser Thr Glu
             20                  25                  30

Ser Gly Gly Ala Gly Glu Ser Gln Glu Asp Met Phe Ala Lys Leu Lys
         35                  40                  45

Glu Lys Leu Phe Asn Glu Ile Asn Lys Ile Pro Leu Pro Pro Trp Ala
     50                  55                  60

Leu Ile Ala Ile Ala Val Val Ala Gly Leu Leu Leu Thr Cys Cys
 65                  70                  75                  80

Phe Cys Ile Cys Lys Lys Cys Cys Cys Lys Lys Lys Asn Lys Lys
                 85                  90                  95

Glu Lys Gly Lys Gly Met Lys Asn Ala Met Asn Met Lys Asp Met Lys
            100                 105                 110

Gly Gly Gln Asp Asp Asp Asp Ala Glu Thr Gly Leu Thr Glu Gly Glu
        115                 120                 125

Gly Glu Gly Glu Glu Glu Lys Glu Pro Glu Asn Leu Gly Lys Leu Gln
        130                 135                 140
```

-continued

```
Phe Ser Leu Asp Tyr Asp Phe Gln Ala Asn Gln Leu Thr Val Gly Val
145                 150                 155                 160

Leu Gln Ala Ala Glu Leu Pro Ala Leu Asp Met Gly Gly Thr Ser Asp
                165                 170                 175

Pro Tyr Val Lys Val Phe Leu Leu Pro Asp Lys Lys Lys Tyr Glu
            180                 185                 190

Thr Lys Val His Arg Lys Thr Leu Asn Pro Ala Phe Asn Glu Thr Phe
            195                 200                 205

Thr Phe Lys Val Pro Tyr Gln Glu Leu Gly Gly Lys Thr Leu Val Met
        210                 215                 220

Ala Ile Tyr Asp Phe Asp Arg Phe Ser Lys His Asp Ile Ile Gly Glu
225                 230                 235                 240

Val Lys Val Pro Met Asn Thr Val Asp Leu Gly Gln Pro Ile Glu Glu
                245                 250                 255

Trp Arg Asp Leu Gln Gly Gly Glu Lys Glu Glu Pro Glu Lys Leu Gly
                260                 265                 270

Asp Ile Cys Thr Ser Leu Arg Tyr Val Pro Thr Ala Gly Lys Leu Thr
            275                 280                 285

Val Cys Ile Leu Glu Ala Lys Asn Leu Lys Lys Met Asp Val Gly Gly
        290                 295                 300

Leu Ser Asp Pro Tyr Gly Lys Ile His Leu Met Gln Asn Gly Lys Arg
305                 310                 315                 320

Leu Lys Lys Lys Lys Thr Thr Val Lys Lys Lys Thr Leu Asn Pro Tyr
                325                 330                 335

Phe Asn Glu Ser Phe Ser Phe Glu Ile Pro Phe Glu Gln Ile Gln Lys
                340                 345                 350

Val Gln Val Val Val Thr Val Leu Asp Tyr Asp Lys Leu Gly Lys Asn
                355                 360                 365

Glu Ala Ile Gly Lys Ile Phe Val Gly Ser Asn Ala Thr Gly Thr Glu
        370                 375                 380

Leu Arg His Trp Ser Asp Met Leu Ala Asn Pro Arg Arg Pro Ile Ala
385                 390                 395                 400

Gln Trp His Ser Leu Lys Pro Glu Glu Glu Val Asp Ala Leu Leu Gly
                405                 410                 415

Lys Asn Lys
```